US007041466B2

(12) United States Patent
Kaltenboeck et al.

(10) Patent No.: US 7,041,466 B2
(45) Date of Patent: May 9, 2006

(54) MOUSE DISEASE MODEL FOR EVALUATION OF PROPHYLACTIC AND THERAPEUTIC TREATMENTS OF *CHLAMYDIA*

(75) Inventors: Bernhard Kaltenboeck, Auburn, AL (US); Jin Huang, Chestnut Hill, MA (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 10/632,426

(22) Filed: Aug. 1, 2003

(65) Prior Publication Data
US 2004/0071634 A1   Apr. 15, 2004

Related U.S. Application Data

(60) Provisional application No. 60/401,070, filed on Aug. 5, 2002.

(51) Int. Cl.
*G01N 33/554* (2006.01)
(52) U.S. Cl. .......................... 435/7.32; 435/4; 435/9.1; 435/9.2
(58) Field of Classification Search .................. 435/4, 435/7.32
See application file for complete search history.

(56) References Cited

U.S. PATENT DOCUMENTS 5,324,668 A    6/1994 Macri

OTHER PUBLICATIONS

Campbell, L.A. et al. 1998. Preclinical models for*Chlamydia pneumoniae* and cardiovascular disease: hypercholesterolemic mice. Clin. Microbial. Infect. 4(supp. 4): S23-S32.*
Yang, Z. et al. 1993. A Mouse Model of *Chlamydia pneumoniae* Strain TWAR Pneumonitis. Infect. Immun. 61(5): 2037-2040.*
Huang, J. et al. Mar. 19, 2002. The quantity of nitric oxide relesaed by macrophages regulates *Chlamydia*-induced disease. P.N.A.S. 99(6): 3914-3919.*
Allione, et al., "Nitric Oxide Suppresses Human T Lymphocyte Proliferation Through IFN-γ-Dependent and IFN-γ-Independent Induction of Apoptosis," *The Journal of Immunology*, 1999, pp. 4182-4191, vol. 163.
Chang, et al., "Arginase Modulates Nitric Oxide Production in Activated Macrophases," *Am. J. Physiol.*, 1998, pp. H342-H348.
Dalton, et al., "Interferon γ Eliminates Responding CD4 T Cells during Mycobacterial Infection by Inducing Apoptosis of Activated CD4 T Cells," *J. Exp. Med.*, 2000, pp. 117-122, vol. 192(1).
Detmers, et al., "Deficiency in Inducible Nitric Oxide Synthase Results in Reduced Atherosclerosis in Apolipoprotein E-Deficient Mice," *The Journal of Immunology*, 2000, pp. 3430-3435, vol. 165.

Diefenbach, et al., "Requirement for Type 2 NO Synthase for IL-12 Signaling in Innate Immunity," *Science*, 1999, pp. 951-955, vol. 284.
Gantt, et al., "Oxidative Responses of Human and Murine Macrophages During Phagocytosis of *Leishmania chagasi*," *The Journal of Immunology*, 2001, pp. 893-901, vol. 167.
Gotoh, T. and Morj, M., "Arginase II Downregulates Nitric Oxide (NO) Production and Prevents NO-mediated Apoptosis in Murine Macrophage-derived RAW 264.7 Cells," *The Journal of Cell Biology*, 1999, pp. 427-434, vol. 144, No. 3.
Guo, et al., "Molecular Mechanisms of Increased Nitric Oxide (NO) in Asthma: Evidence for Transcriptional and Post-Translational Regulation of NO Synthesis," *The Journal of Immunology*, 2000, pp. 5970-5980, vol. 164.
Herrick, C.A. and Bottomly, K., "To Respond or Not To Respond: T Cells in Allergic Asthma," *Nature Reviews/Immunology*, 2003, pp. 1-8, vol. 3.
Holland, et al., "Conjunctival Scarring in Trachoma Is Associated with Depressed Cell-Mediated Immune Responses to *Chlamydial* Antigens," *The Journal of Infectious Diseases*, 1993, pp. 1528-1531, vol. 168.
Hu, et al., "The Artherogenic Effects of *Chlamydia* are Eependent on Serum Cholesterol and Specific to *Chlamydia pneumoniae*," *Journal of Clinical Investigation.*, 1999, pp. 747-753, vol. 103(5).
Huang, et al., "Nitric Oxide Regulates Th1 Cell Development Through the Inhibition of IL-12 Synthesis by Macrophages," *Eur. J. Immunol.*, 1998, pp. 4062-4070, vol. 28.
Huang, et al., "IL-12 Administered During *Chlamydia psittaci* Lung Infection in Mice Confers Immediate and Long-Term Protection and Reduces Macrophage Inflammatory Protein-2 Level and Neutrophil Infiltration in Lung Tissue," *The Journal of Immunology*, 1999, pp. 2217-2226, vol. 162.
Huang, et al., "The Quantity of Nitric Oxide Released by Macrophages Regulates *Chlamydia*-induced Disease," *PNAS*, 2002, pp. 3914-3919, vol. 99(6).
Igietseme, et al., "Resolution of Murine *Chlamydial* Genital Infection by the Adoptive Transfer of a Biovar-Specific, TH$_1$ Lymphocyte Clone," *Regional Immunology*, 1993, pp. 317-324, vol. 5.

(Continued)

*Primary Examiner*—Jennifer E. Graser
(74) *Attorney, Agent, or Firm*—Alston & Bird LLP

(57) ABSTRACT

Compositions and methods are provided for evaluating the progress of disease induced by infection with *Chlamydia* spp. Specifically, the invention provides a mouse lung disease model of infection with *Chlamydia* spp. bacteria. The compositions and methods of the invention find use in evaluating the efficacy of vaccines and other therapeutic or prophylactic treatments of *Chlamydia*-induced disease.

6 Claims, 5 Drawing Sheets

OTHER PUBLICATIONS

Figure 3:
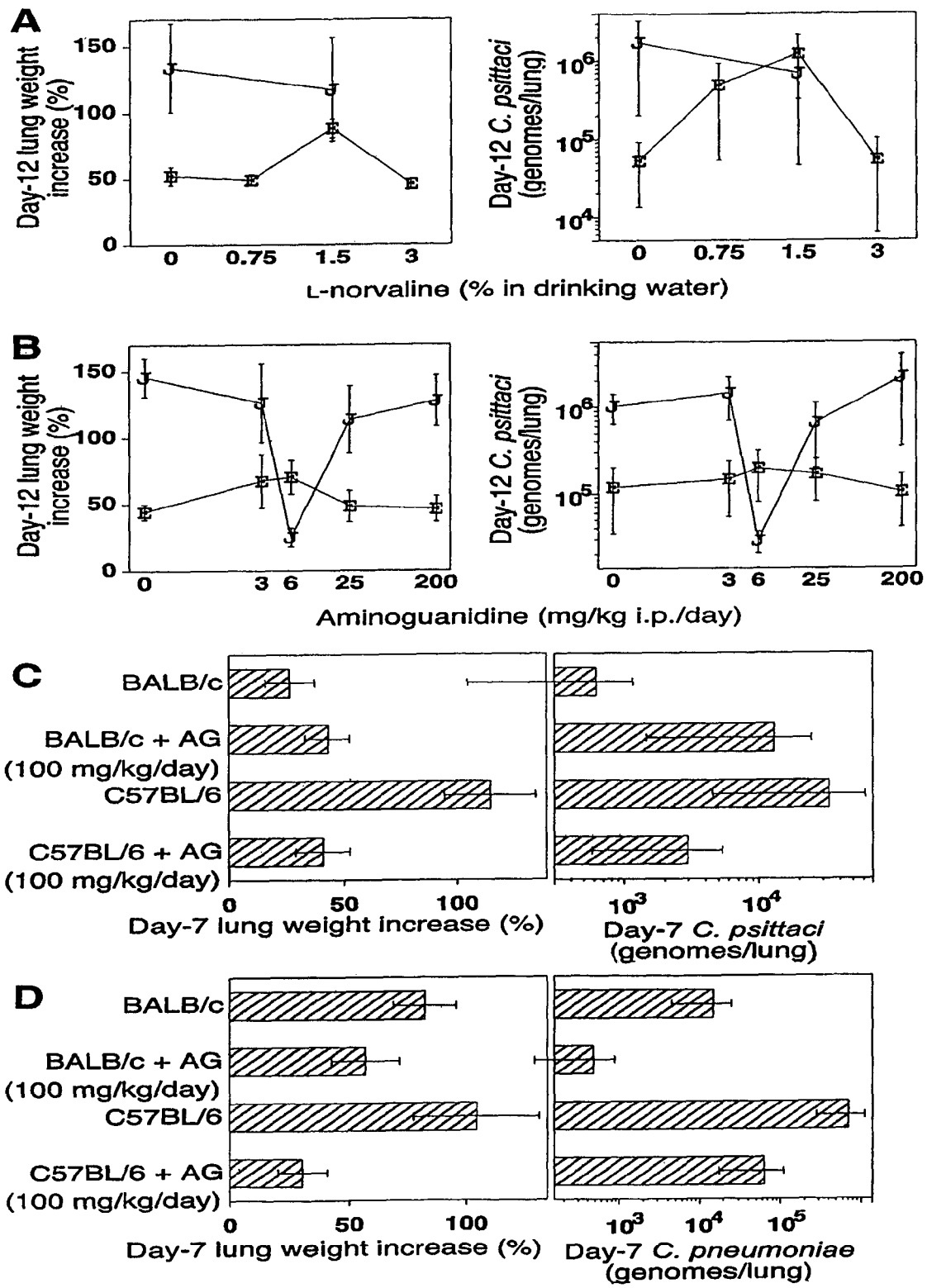

Igietseme, et al., "Chlamydial Infection in Inducible Nitric Oxide Synthase Knockout Mice," *Infection and Immunity*, 1998, pp. 1282-1286, vol. 66(4).

Mori, M. and Gotoh, T., "Relationship between Arginase Activity and Nitric Oxide Production," Chapter 12, *Nitric Oxide Biology and Pathiobiology*, 2000, Chapter 12, pp. 199-208.

Jackson, et al., "Specificity of Detection of *Chlamydia pneumoniae* in Cardiovascular Atheroma," *American Journal of Pathology*, 1997, pp. 1785-1790, vol. 150(5).

Kaltenböck, et al., "Genetically Determined Vigorous Innate Immunity is Associated with Protection Against Primary Chlamydial Lung Infection in Mice, but with Profound Disease Exacerbation in Reinfection," *Chlamydial Infections*, Proceedings of the Ninth International Symposium on Human *Chlamydial* Infection, Jun. 21-26, 1998, pp. 403-406.

Lyons, et al., "Molecular Cloning and Functional Expression of an Inducible Nitric Oxide Synthase from a Murine Macrophage Cell Line," *The Journal of Biological Chemistry*, 1992, pp. 6370-6374, vol. 267(9).

Macmicking, et al., "Nitric Oxide and Macrophage Function," *Annu. Rev. Immunol.*, 1997, pp. 323-350, vol. 15.

Magee, et al., "*Chlamydia trachomatis* Pneumonia in the Severe Combined Immunodeficiency (SCID) Mouse," *Regional Immunology*, 1993, pp. 305-311, vol. 5(6).

Mills, et al., "M-1/M-2 Macrophages and the Th1/Th2 Paradigm," *The Journal of Immunology*, 2000, pp. 6166-6173, vol. 164.

Moazed, et al., "Evidence of Systemic Dissemination of *Chlamydia pneumoniae* via Macrophages in the Mouse," *The Journal of Infectious Diseases*, 1998, pp. 1322-1325, vol. 177.

Moazed, et al., "*Chlamydia pneumoniae* Infection Accelerates the Progression of Atherosclerosis in Apolipoprotein E-Deficient Mice," *The Journal of Infectious Diseases*, 1999, pp. 238-241, vol. 180.

Morrison, et al., "Gene Knockout Mice Establish a Primary Protective Role for Major Hisocompatibility Complex Class II-Restricted Responses in *Chlamydia trachomatis* Genital Tract Infection," *Infection and Immunity*, 1995, pp. 4661-4668, vol. 63(12).

Munder, et al., "Th1/Th2-Regulated Expression of Arginase Isoforms in Murine Macrophages and Dendritic Cells," *The Journal of Immunology*, 1999, pp. 3771-3777, vol. 163.

Oswald, et al., "Low Response of BALB/c marophages to Priming and Activating Signals," *Journal of Leukocyte Biology*, 1992, pp. 315-322, vol. 52.

Perry, et al., "Neither Interleukin-6 nor Inducible Nitric Oxide Synthase is Required for Clearance of *Chlamydia trachomatis* from the Murine Genital Tract Epithelium," *Infection and Immunity*, 1998, pp. 1265-1269, vol. 66(3).

Ramsey, et al., "*Chlamydia trachomatis* Persistance in the Female Mouse Genital Tract: Inducible Nitric Oxide Synthase and Infection Outcome," *Infection and Immunity*, 2001, pp. 5131-5137, vol. 69(8).

Rank, R.G., "Models of Immunity," *Chlamydia: Intracellular Biology, Pathogenesis, and Immunity*, 1999, Chapter 9, pp. 239-295.

Ross, R., "Atherosclerosis—An Inflammatory Disease," *Mechanisms of Disease*, 1999, pp. 115-126, vol. 340(2).

Rottenberg, et al., "Role of Innate and Adaptive Immunity in the Outcome of Primary Infection with *Chlamydia pneumoniae*, as Analyzed in Genetically Modified Mice," *The Journal of Immunology*, 1999, pp. 2829-2836, vol. 162.

Schachter, J., "Infection and Disease Epidemiology," *Chlamydia: Intracellular Biology, Pathogenesis, and Immunity*, 1999, Chapter 6, pp. 139-169.

Schwacha, M.G. and Eisenstein, T.K., "Interleukin-12 is Critical for Induction of Nitric Oxide-Mediated Immunosuppression following Vaccination of Mice with Attenuated *Salmonella typhimurium*," *Infection and Immunity*, 1997, pp. 4897-4903, vol. 65(12).

Schwacha, et al., "*Salmonella typhimurium* Infection in Mice Induces Nitric Oxide-Mediated Immunosuppression through a Natural Killer Cell-Dependent Pathway," *Infection and Immunity*, 1998, pp. 5862-5866, vol. 66(12).

Stevenson, et al., "Genetic Linkage of Resitance to *Listeria Monocytogenes* with Macrophage Inflammatory Responses," *The Journal of Immunology*, 1981, pp. 402-407, vol. 127(2).

Tews, J.K. and Harper, A.E., "Tissue Amino Acids in Rats Fed Norlelucine, Norvaline, Homoarginine or Other Amino Acid Analogues," *J. Nutr.*, 1986, pp. 1464-1472, vol. 116(8).

Wiltshire, et al., "Genome-wide Single-nucleotide Polymorphism Analysis Defines Haplotype Patterns in Mouse," *PNAS*, 2003, pp. 3380-3385, vol. 100(6).

Wright, et al., "Infectious Agents Are Not Necessary for Murine Atherogenesis," *J. Exp. Med.*, 2000, pp. 1437-1441, vol. 191(8).

Xie, et al., "Cloning and Characterization of Inducible Nitric Oxide Synthase from Mouse Macrophages," *Science*, 1992, pp. 226-228, vol. 256.

* cited by examiner

SEQUENCE LISTING

<160> NUMBER OF SEQ ID NOS: 13

<210> SEQ ID NO 1
<211> LENGTH: 27
<212> TYPE: DNA
<213> ORGANISM: Artificial Sequence
<220> FEATURE:
<223> OTHER INFORMATION: C. pneumoniae-specific probe

<400> SEQUENCE: 1
cacattaagt tcttcaactt taggttt                                27

<210> SEQ ID NO 2
<211> LENGTH: 27
<212> TYPE: DNA
<213> ORGANISM: Artificial Sequence
<220> FEATURE:
<223> OTHER INFORMATION: Beta-actin sense PCR primer

<400> SEQUENCE: 2
ctcctcctga gcgcaagtac tctgtgt                                27

<210> SEQ ID NO 3
<211> LENGTH: 26
<212> TYPE: DNA
<213> ORGANISM: Artificial Sequence
<220> FEATURE:
<223> OTHER INFORMATION: Beta-actin antisense PCR primer

<400> SEQUENCE: 3
gtgcacgatg gaggggccgg actcat                                 26

<210> SEQ ID NO 4
<211> LENGTH: 25
<212> TYPE: DNA
<213> ORGANISM: Artificial Sequence
<220> FEATURE:
<223> OTHER INFORMATION: NOS2 sense PCR primer

<400> SEQUENCE: 4
cacttggatc aggaacctga agccc                                  25

<210> SEQ ID NO 5
<211> LENGTH: 25
<212> TYPE: DNA
<213> ORGANISM: Artificial Sequence
<220> FEATURE:
<223> OTHER INFORMATION: NOS2 antisense PCR primer

<400> SEQUENCE: 5
ctttgtgctg ggagtcatgg agccg                                  25

<210> SEQ ID NO 6
<211> LENGTH: 25
<212> TYPE: DNA
<213> ORGANISM: Artificial Sequence
<220> FEATURE:
<223> OTHER INFORMATION: Arginase I sense PCR primer

<400> SEQUENCE: 6
agctggggat tggcaaggtg atgga                                  25

<210> SEQ ID NO 7
<211> LENGTH: 28

```
<212> TYPE: DNA
<213> ORGANISM: Artificial Sequence
<220> FEATURE:
<223> OTHER INFORMATION: Arginase I antisense PCR primer

<400> SEQUENCE: 7
agccctgtct tgtaaatttc ttctgtga                                  28

<210> SEQ ID NO 8
<211> LENGTH: 27
<212> TYPE: DNA
<213> ORGANISM: Artificial Sequence
<220> FEATURE:
<223> OTHER INFORMATION: Arginase II sense PCR primer

<400> SEQUENCE: 8
ctgtagctat agtcggagcc cctttct                                   27

<210> SEQ ID NO 9
<211> LENGTH: 22
<212> TYPE: DNA
<213> ORGANISM: Artificial Sequence
<220> FEATURE:
<223> OTHER INFORMATION: Arginase II antisense PCR primer

<400> SEQUENCE: 9
gtggcatccc aacctggaga gc                                        22

<210> SEQ ID NO 10
<211> LENGTH: 22
<212> TYPE: DNA
<213> ORGANISM: Artificial Sequence
<220> FEATURE:
<223> OTHER INFORMATION: NOS2 FRET-qPCR downstream primer

<400> SEQUENCE: 10
catcctcatt gggcctggta cg                                        22

<210> SEQ ID NO 11
<211> LENGTH: 20
<212> TYPE: DNA
<213> ORGANISM: Artificial Sequence
<220> FEATURE:
<223> OTHER INFORMATION: NOS2 FRET-qPCR upstream primer

<400> SEQUENCE: 11
tgaggacccc ttccagcctt                                           20

<210> SEQ ID NO 12
<211> LENGTH: 28
<212> TYPE: DNA
<213> ORGANISM: Artificial Sequence
<220> FEATURE:
<223> OTHER INFORMATION: IFN-gamma sense PCR primer

<400> SEQUENCE: 12
tgccaagttt gaggtcaaca acccacag                                  28

<210> SEQ ID NO 13
<211> LENGTH: 25
<212> TYPE: DNA
<213> ORGANISM: Artificial Sequence
<220> FEATURE:
<223> OTHER INFORMATION: IFN-gamma antisense PCR primer
```

```
<400> SEQUENCE: 13
gcgactcctt ttccgcttcc tgagg                                              25
```

MOUSE DISEASE MODEL FOR EVALUATION OF PROPHYLACTIC AND THERAPEUTIC TREATMENTS OF *CHLAMYDIA*

CROSS-REFERENCE TO RELATED APPLICATIONS

This application claims the benefit of U.S. Provisional Application No. 60/401,070, filed Aug. 5, 2002.

FEDERALLY SPONSORED RESEARCH OR DEVELOPMENT

This research underlying this invention was supported in part with funds from the National Institute of Health, grant number PHS-1-R29-A138977. The United States Government may have an interest in the subject matter of the invention.

FIELD OF THE INVENTION

The present invention relates to the field of disease models. Specifically, the present invention relates to the evaluation of infection with *Chlamydia* spp. and to the evaluation of therapeutic and prophylactic treatments of *Chlamydia*-induced disease.

BACKGROUND OF THE INVENTION

Intracellular bacteria of the genus *Chlamydia* are among the most common human pathogens and are the leading bacterial cause of sexually transmitted disease and preventable blindness. See Schachter, J. (1999) in *Chlamydia*, ed. Stephens, R. S. (Am. Soc. Microbiol., Washington, D.C.), pp. 139–169. Over the last decade, *Chlamydia pneumoniae* has been identified in a high proportion of atherosclerotic lesions, suggesting a role for chlamydial infection in coronary heart disease. See Saikku et al. (1988) *Lancet* ii: 983–986; Jackson et al. (1997) *Am. J. Pathol.* 150: 1785–1790. Recently, *Chlamydia* has been detected in brain lesions of patients with Alzheimer's disease. See Balin et al. (1998) *Med. Microbiol. Immunol.* 187: 23–42.

In early trials, vaccination against *Chlamydia trachomatis* surprisingly increased rate and severity of the naturally acquired chlamydial eye disease, trachoma, whereas in other trials the rate of disease declined but the severity increased. See Ward, M. E. (1999) in *Chlamydia*, ed. Stephens, R. S. (Am. Soc. Microbiol., Washington, D.C.) pp. 171–210. The high seroprevalence of *C. pneumoniae* infection is not accompanied by equally high organism isolation or disease rates. See Saikku, P. (1998) in *Chlamydial Infections: Proceedings of the Ninth International Symposium on Human Chlamydial Infection, Napa, Calif., June* 1998, ed. Stephens, R. S. (Univ. of California Press, Berkeley), pp. 145–154. Collectively, these data support the notion that some individuals react with increased sensitivity to repeated exposure to chlamydial agents whereas others develop a protective response. Similarly, animal studies indicate that genetic determinants of the host response to *Chlamydia* spp. play a decisive role in the outcome of chlamydial infection. See Yang et al. (1996) *J. Immunol.* 156: 4338–4344.

Thus, there is a need to identify and study causes of unfavorable reactions to chlamydial infection. Accordingly, there is a need for non-human disease models which are suitable for evaluating the effects of therapeutic and prophylactic treatments on chlamydial infection.

SUMMARY OF THE INVENTION

Compositions and methods are provided for evaluating the progress of disease induced by infection with *Chlamydia* spp. and for evaluating the efficacy of prophylactic and therapeutic treatments of such disease. Specifically, the invention provides a mouse lung disease model of infection and disease produced by *Chlamydia* spp. bacteria. The compositions and methods of the invention find use in studying the environmental and genetic factors affecting *Chlamydia*-induced disease as well as in evaluating the efficacy of therapeutic and prophylactic treatments of such disease, including diet and vaccination.

BRIEF DESCRIPTION OF THE DRAWING(S)

Figure 1:
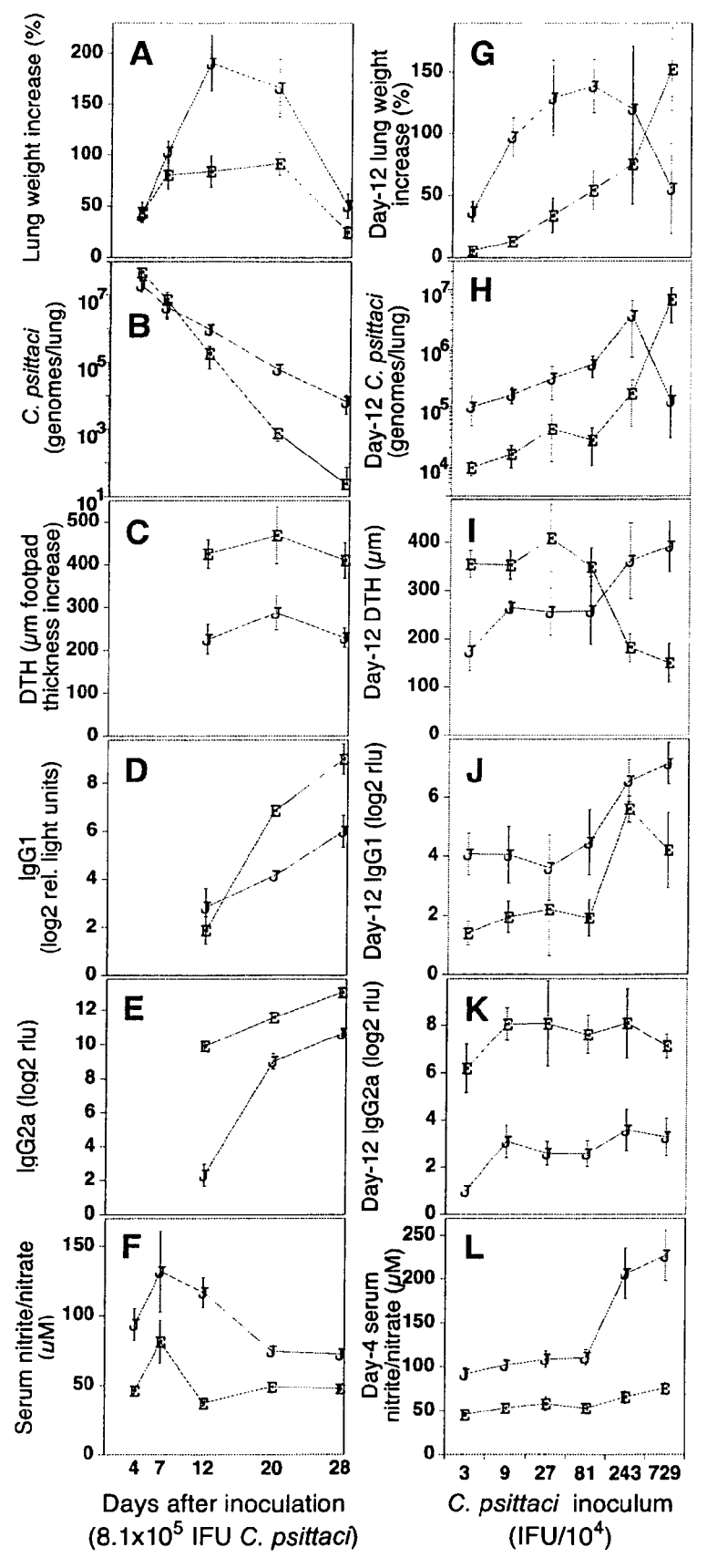

FIG. 1: (see Example 1) Increased NO (nitric oxide) production in C57BL/6 mice after chlamydial infection is associated with enhanced disease and suppressed immunity. C57BL/6 mice (designated by letter "J") or BALB/c mice (designated by letter "E") were infected intranasally with $8.1 \times 10^5$ inclusion-forming units (IFU) *C. psittaci* (panels A–F) or a series of inocula (panels G–L) and killed on the indicated day after inoculation (A–F), on day 12 when interstitial pneumonia was at maximal severity (G–K), or on day 4 (L). Panels A and G show the time and dose dependency of chlamydial pneumonia expressed as lung weight increase over that of mock-infected mice (n=12–18, combined data of four experiments, ±SEM). BALB/c mice showed an 80% lung weight increase whereas C57BL/6 mice had a 190% increase over the average naïve lung weight of 116.3 mg. Panels B and H show total chlamydial lung burden expressed as *C. psittaci* genomes per lung determined by FRET-qPCR. Panels C and I show the DTH (delayed-type hypersensitivity) response to *C. psittaci* as an increase in footpad thickness 24 hours after antigen injection. Panels D, E, J, and K show the levels of IgG1 and IgG2a antibodies against *C. psittaci*. Panels F and L show the total serum nitrite/nitrate as a parameter of cumulative NO production. Dependency of NO production in response to the chlamydial inoculum is shown for day 4, at the maximum of the early, innate response to the chlamydial infection.

FIG. 2: (see Example 1) BALB/c mice express arginase II in response to chlamydial infection more rapidly and at higher levels than C57BL/6 mice. BALB/c mice (designated by letter "E") or C57BL/6 mice (designated by letter "J") were intranasally infected with a series of *C. psittaci* inocula (A–D) and transcripts in lung tissue were determined on day 4 (n=12–18, combined data of three experiments). Panels E-H show transcript levels in peritoneal macrophages of BALB/c mice that were infected (designated by letter "E") or mock-infected (designated by letter "C") or C57BL/6 mice that were infected (designated by letter "J") or mock-infected (designated by letter "H") with *C. psittaci*. Specific mRNA levels were determined by RT-qPCR and were plotted as transcripts per $10^5$ β-actin transcripts as a function of time (n=6, one of two experiments is shown). Panels A and E show NOS2 transcripts in *Chlamydia*-infected lung tissue or macrophages; panels B and F show arginase I transcripts; panels C and G show arginase II transcripts; and panels D and H show the ratio of arginase II to arginase I transcripts.

FIG. 3: (see Example 1). Modulation of NO production with arginase and NOS2 inhibitors reversed chlamydial disease phenotypes in an inhibitor-dose-dependent manner in primary and secondary infection with *C. psittaci* or *C. pneumoniae*. (A) Mice were intranasally inoculated with $8.1\times10^5$ IFU *C. psittaci* and received the arginase inhibitor L-norvaline in drinking water. L-norvaline (1.5%) application significantly increased serum nitrite/nitrate and chlamydial lung disease in BALB/c (designated by letter "E"), but not in C57BL/6 mice (designated by letter "J"; $P_{diseaseBalb/c:BALB/c+1.5\% \; L-norvaline}=0.024$; $P_{chlamydiaeBALB/c:BALB/c+1.5\% \; L-norvaline}=0.049$; BALB/c, 62.3 µM day-4 serum nitrite/nitrate±5.9, SEM; BALB/c+1.5% L-norvaline, 123.22±38.8; n=12; P=0.68). Lower or higher application did not change the disease in BALB/c mice (n=8–20, combined data of four experiments). (B) Mice were given the NOS2 inhibitor AG (aminoguanidine) and one day later were intranasally inoculated with $8.1\times10^5$ IFU *C. psittaci*. AG application significantly reduced serum nitrite/nitrate (BALB/c, 48.7 µM day-4 serum nitrite/nitrate±2.7, n=26; C57BL/6, 89.8±7.5, n=26; $P_{BALB/c:C57BL/6}=0.0002$; C57BL/6+6 mg/kg per day AG, 73.2±3.8, n=24, P 0 mgAG:6 mgAG=0.035; C57BL/6+200 mg/kg per day AG, 39.7+/−2.9, n=18, P 0 mgAG:200 mgAG=0.00006). Daily administration of 6 mg AG per kg body mass, but not of higher or lower doses, completely reversed the severe day-12 disease phenotype of C57BL/6 mice to the protected phenotype of BALB/c mice, as measured by lung weight increase or total chlamydial lung burden ($P_{DiseaseC57BL/6:C57BL/6+6 \; mgAG}=0.0000001$, $P_{chlamydiae \; C57BL/6:C57BL/6+6 \; mgAG}=0.002$). BALB/c mice in all dosage groups did not show significant changes in their day-12 disease (n=6–24, combined data of five experiments). (C) Mice received a low $3\times10^4$ IFU *C. psittaci* priming intranasal infection, and 5 weeks later a challenge of $6\times10^6$ IFU *C. psittaci*. A dose of 100 mg/kg AG per day completely abolished disease of C57BL/6 mice on day 7 after secondary infection ($P_{DiseaseC57BL/6:C57BL/6+AG}=0.003$, $P_{chlamydiaeC57BL/6:C57BL/6+AG}=0.35$). BALB/c disease is marginally increased, and chlamydial burden is substantially, but not significantly, higher (N=10, combined data of two experiments). (D) Mice primed with $3\times10^5$ IFU *C. pneumoniae* were challenged 5 weeks later with $3\times10^7$ IFU *C. pneumoniae*. With AG (aminoguanidine) treatment, both mouse strains are free of gross lung disease and show reduced chlamydial lung loads (N=10, combined data of two experiments, $P_{DiseaseC57BL/6:C57BL/6+AG}=0.019$, $P_{chlamydiaeC57BL/6:C57BL/6+AG}=0.14$; $P_{Disease \; BALB/c: \; BALB/c+AG}=0.21$; $P_{chlamydiaeBALB/c:BALB/c+AG}=0.12$).

Figure 4:
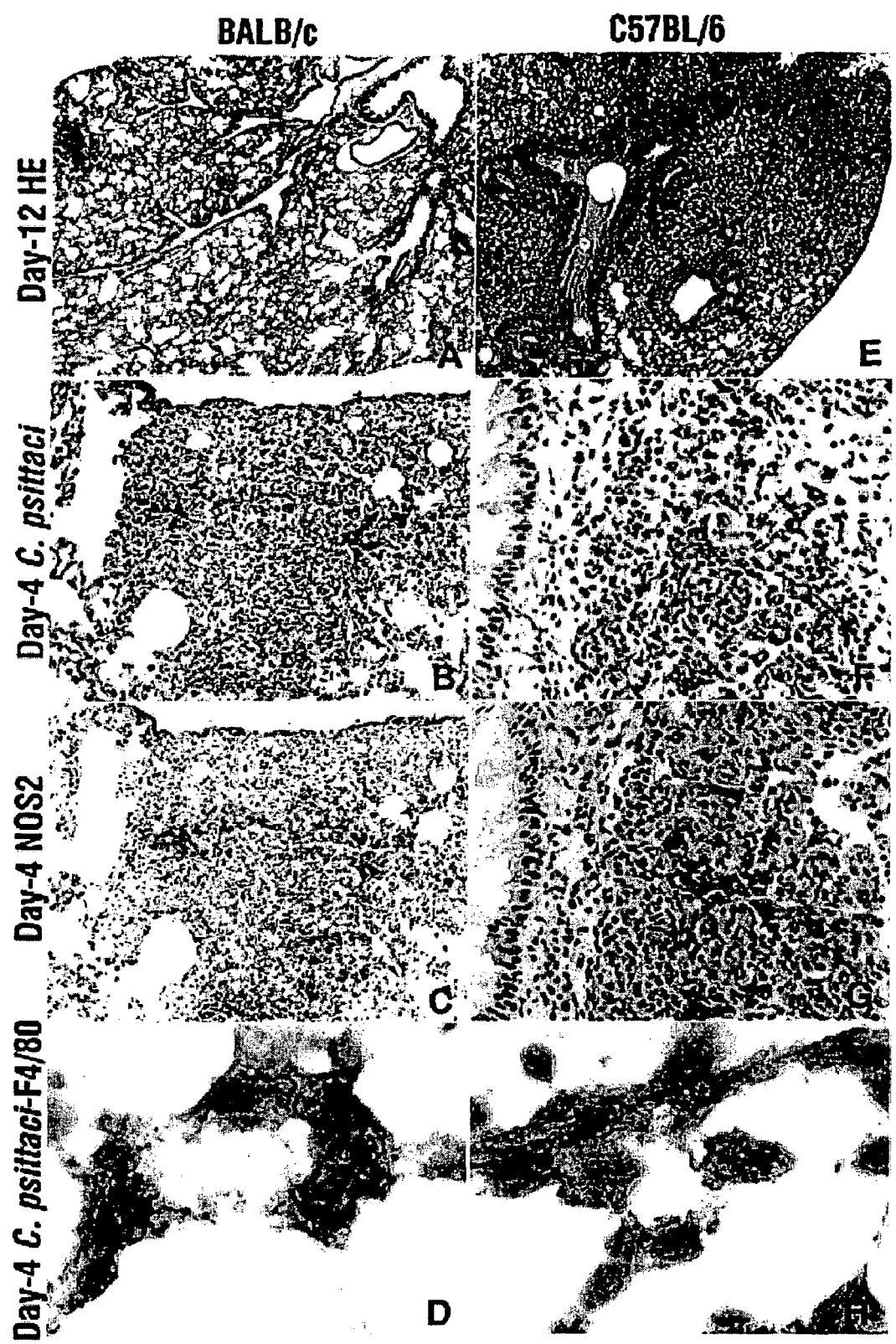

FIG. 4: (see Example 3) Both mouse strains produced NO by NOS2 expressed in *Chlamydia*-infected macrophages. Mice infected with $8.2\times10^5$ IFU *C. psittaci* were sacrificed on day 12 (panels A and E; maximum disease) or day 4 (B–D and F–H; maximum innate response) and lung sections were stained. Panels A and E showed hematoxylin and eosin staining on day 12 (magnification, ×100). Lungs of BALB/c mice (A) appeared essentially normal with minor diffuse interstitial and few small foci of peribronchiolar mononuclear cell infiltrate. In contrast, lungs of C57BL/6 mice (E) showed extensive mononuclear cell infiltrates and large areas of lung consolidation. Panels B, C, F, and G show serial sections of lung from day 4 with foci of mononuclear infiltrates from BALB/c mice (B and C; magnification, ×100) and C57BL/6 mice (F and G; magnification, ×400). These sections were stained for *C. psittaci* (B and F) or NOS2 (C and G). Chlamydial antigen and NOS2 colocalized to cells of macrophage morphology in both mouse strains. These cells were positive for macrophage maturation antigen F4/80 in cryosections (D and H), and antibodies that recognize chlamydiae or NOS2 colocalized with the F4/80 antigen. Panels D and H show cryosections (magnification, ×1,000) of lung inflammatory foci of BALB/c (D) and C57BL/6 mice (H) double-immunostained for *C. psittaci* and F4/80 macrophage maturation antigen; *C. psittaci* staining and F8/80 staining colocalized. Double-immunostaining of cryosections for NOS2 and F4/80 or for *C. psittaci* and NOS2 resulted in virtually identical patterns of color distribution.

Figure 5:
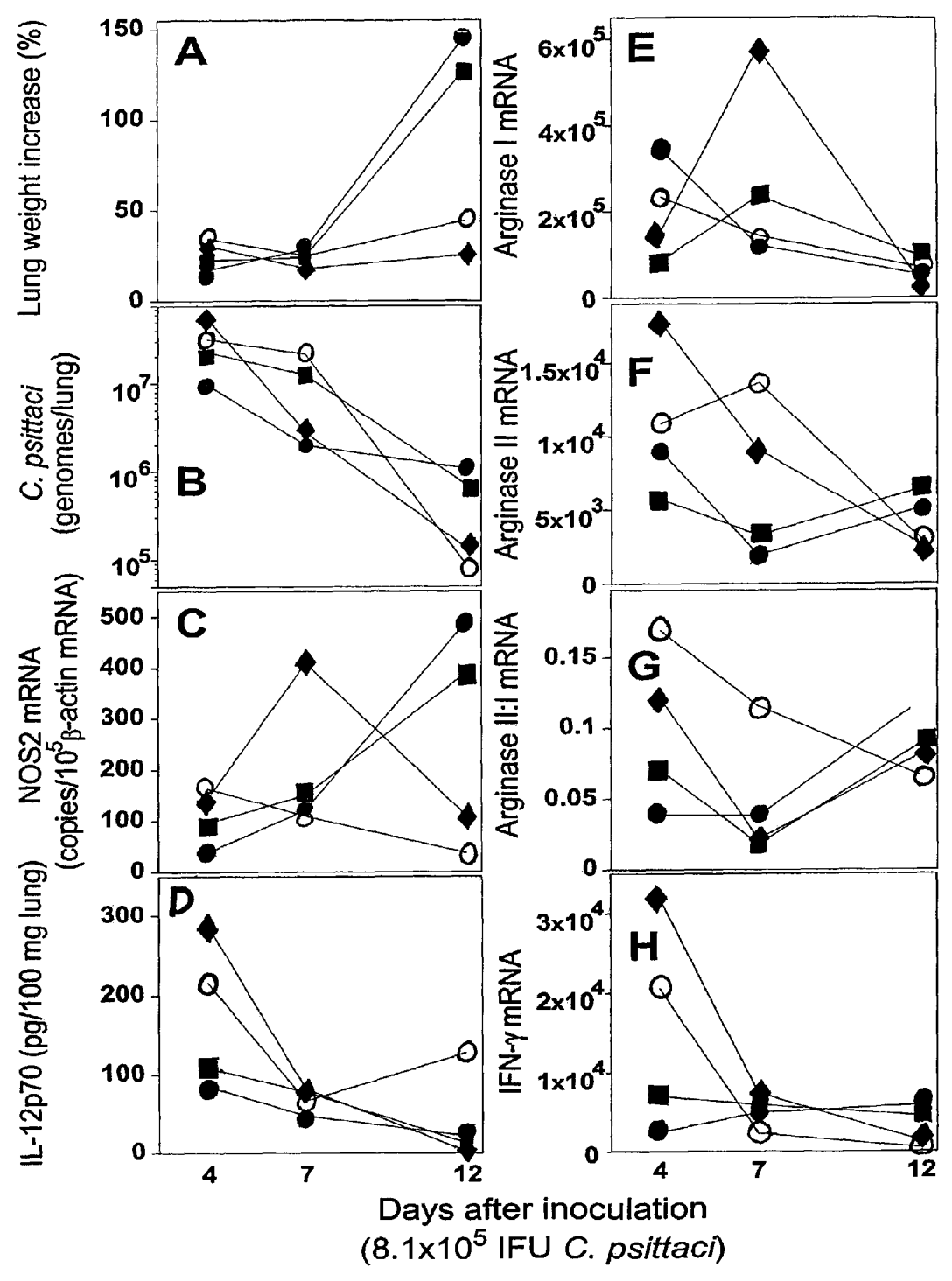

FIG. 5: (see Example 1) Optimum AG (aminoguanidine) treatment level protects C57BL/6 mice and increases early arginase II, IFN-γ, and IL-12p70 and reduces early arginase I expression. Mice were intranasally inoculated with $8.1\times10^5$ IFU *C. psittaci*. C57BL/6 mice (solid circles) and BALB/c mice (open circles) were intraperitoneally injected with PBS. Groups of C57BL/6 mice received AG daily at a dose of 6 mg/kg (solid diamonds) or 200 mg/kg (solid squares), and the time course of mRNA and IL-12p70 levels in lung tissue was determined (n=10, combined data of two experiments).

Panel A of FIG. 5 shows lung weight increase. Untreated and 200 mg/kg AG-treated C57BL/6 mice developed severe day-12 disease whereas 6 mg/kg AG-treated C57BL/6 and BALB/c mice were protected ($P_{C57BL/6:C57BL/6+6 \; mg \; AG}=0.017$). Panel B of FIG. 5 shows total *C. psittaci* lung burden. On day 4, untreated C57BL/6 mice had significantly lower chlamydial lung burdens than all other mice ($P_{C57BL/6:C57BL/6+6 \; mg \; AG}= 0.007$). On day 7, BALB/c and 200 mg/kg AG-treated C57BL/6 mice had higher chlamydial burdens than untreated and 6 mg/kg AG-treated C57BL/6 mice ($P_{C57BL/6:C57BL/16+200 \; mgAG}=0.077$). After day 7, BALB/c and 6 mg/kg AG-treated C57BL/6 mice eliminated chlamydiae significantly more rapidly from lungs than untreated and 200 mg/kg AG-treated C57BL/6 mice ($P_{C57BL/6:C57BL/6+6 \; Ag \; AG}=0.000001$). Panel C shows the level of NOS2 transcripts. NOS2, arginase I, and arginase II transcript levels on days 4 and 12 in 6 mg/kg AG-treated C57BL/6 mice resembled those of BALB/c mice and were not significantly higher on day 7 than those of all other groups ($P_{C57BL/6:C57BL/6+6 \; mgAG}=0.54$). Untreated and 200 mg/kg AG-treated C57BL/6 mice had similar day-12 transcript levels that differ significantly from 6 mg/kg AG-treated C57BL/6 and BALB/c mice ($P_{C57BL/6:C57BL/6+6 \; mgAG}=0.037$). Panel D shows IL-12p70 expression. On day 4, BALB/c and 6 mg/kg AG-treated C57BL/6 mice had significantly higher IL-12p70 and IFN-γ transcript lung levels than untreated or 200 mg/kg AG-treated C57BL/6 mice ($P_{C57BL/6:C57BL/6+6 \; mgAG}=0.0006$). (E) Arginase I transcripts. (F) Arginase II transcripts. (G) Ratio of arginase II to arginase I transcripts ($P_{day-4C57BL/6:C57BL/6+6 \; mgG}=0.011$). (H) IFN-γ transcripts ($P_{day4C57BL/6:C57BL/6+6 \; mgAG}=0.015$).

DETAILED DESCRIPTION OF THE INVENTION

The invention is drawn to compositions and methods for the evaluation of infection with *Chlamydia* spp. Specifically, the invention provides a mouse lung disease model of infection with *Chlamydia* spp. bacteria. The compositions and methods of the invention find use in evaluating the efficacy therapeutic and prophylactic treatments of *Chlamydia*-induced disease. The compositions and methods of the invention provide optimal control of variables influencing disease outcome in pulmonary infection of mice by *Chlamydia* spp. and thus minimize experimental variance. In this manner, the invention provides accurate and reliable models for the identification and characterization of protective and prophylactic agents against chlamydial disease, such as, for example, vaccines. The invention also provides models for the evaluation of various treatments for chlamydial disease.

While the invention is not bound by a particular mechanism of operation, we have shown that the quantity of nitric oxide released by macrophages regulates *Chlamydia*-induced disease (see Huang et al. (2002) *Proc. Nat'l. Acad. Sci. USA* 99: 3914–3919). The general nature of the mechanisms involved in response to *Chlamydia* lung infections suggests that these mechanisms are involved not only in lung disease, but in all infections with *Chlamydia* spp. Therefore, the mouse models of the invention may be useful in assessing any chlamydial infection.

In some embodiments of the present invention, at least one parameter of *Chlamydia*-induced disease is measured in at least one test mouse exposed to *Chlamydia*. The value of this parameter is measured by analytical methods known in the art or disclosed herein. The value of this parameter is then compared to the value of the same parameter gathered from at least one reference mouse. This comparison allows one of skill to determine whether the *Chlamydia*-induced disease is more severe or less severe in the test mouse than in the reference mouse. It is understood by those of ordinary skill in the art that the parameter value from the test mouse ("test parameter value") and the parameter value from the reference mouse ("reference parameter value") are each measured in mice that are comparable but that differ (i.e., have differences) in at least one aspect which is of interest. For example, the test mouse and the reference mouse may differ in their genetic composition, the dose of *Chlamydia* with which they were treated, the composition of their diet, whether they have been treated with a NOS2 inhibitor, or whether they have been treated with a particular drug. As will be obvious to those of skill in the art, the test mouse and the reference mouse may differ in multiple ways. As will also be obvious to those of skill in the art, the comparison of the test parameter value and the reference parameter value permits evaluation of the consequences of various differences in genetics, treatment, etc. on *Chlamydia*-induced disease and thus provides the mouse model of the present invention. It is further understood that multiple comparisons of test and reference mice, as illustrated by the working examples presented herein, will allow for more reliable conclusions regarding the effects of the differences examined.

Provided is a rational approach for selecting a mouse strain appropriate for evaluation of aspects of chlamydial disease, for example, for evaluation of immune protection mediated by a vaccine against *Chlamydia*. A suitable mouse strain for this purpose has a low innate macrophage inflammatory response to stimulation by bacterial antigens. Such strains are known in the art (see, e.g., Stevenson et al. (1981) *J. Immunol.* 127: 402–407) and include the BALB/c and A/J strains. Such strains produce little nitric oxide (NO) in response to direct stimulation by chlamydial antigens and to co-stimulation by cytokines and chemokines produced by *Chlamydia*-specific immune cells.

In contrast to strains showing a low innate macrophage inflammatory response ("low responders"), "high responder" strains such as C57BL/6J mice produce high amounts of NO when stimulated by bacterial antigens. High amounts of NO induce apoptosis (programmed cell death) in many immune cells in the context of antigen-specific stimulation. Thus, high responder mouse strains will tend to suppress the immune response during challenge infection, including a vaccine-induced response, and will require a relatively long time for elimination of chlamydial organisms. In contrast, low responder strains will not suppress vaccine immunity and thus will be protected by effective vaccines against *Chlamydia* and will eliminate the organisms from the infected lung more rapidly than high responder strains. High responder strains may be treated so that they mimic the responses of low responder strains, as illustrated by the experiments using AG (aminoguanidine) treatment described in Example 1. Thus, further provided is a rational approach for treating high responder strains with appropriate levels of NOS2 inhibiting drugs so that an appropriate level of response may be obtained to accomplish the goals of the invention.

The innate inflammatory responses of macrophages of many important mouse strains is known in the art. See, for example, Stevenson et al. (1981) *J. Immunology* 127: 402–407, entitled "Genetic linkage of resistance to *Listeria monocytogenes* with macrophage inflammatory responses." Table II of Stevenson et al. (1981) lists relative macrophage inflammatory responses of 9 mouse strains. The lowest low responders are optimal for use in *Chlamydia* challenge experiments; as indicated in Stevenson et al. (1981), these strains include BALB/c, A/J, DBA/1J, and DBA/2J. Relative macrophage inflammatory responses of different strains are also reflected in the phylogenetic relationships of haplotype patterns of the mouse genome, as established by Wiltshire et al. (2003) *Proc. Nat'l. Acad. Sci. USA* 100: 3380–3385, entitled "Genome-wide single-nucleotide polymorphism analysis defines haplotype patterns in mouse."

In addition, experiments with different chlamydial species show that particular mouse strains are optimally suited for evaluation of particular chlamydiae. Among strains that are low responders, A/J mice show the lowest macrophage inflammatory response while BALB/c mice have a somewhat more vigorous response. Thus, BALB/c mice are optimal for use in challenge experiments with relatively rapidly multiplying chlamydial species such as *Chlamydia psittaci* (burst size ~900 infectious organisms/infected cell). In contrast, challenge of A/J mice with *C. psittaci* can be performed with only very low infectious doses because even moderately high doses of *C. psittaci* overwhelm the weak innate macrophage inflammatory protection of A/J mice, resulting in frequent death and a very low $LD_{50}$ of *C. psittaci*. However, the weak response of A/J mice makes them well suited for experiments involving the administration of challenge infections or doses of slowly replicating *Chlamydia pneumoniae* (burst size ~300 infectious organisms/infected cell), while BALB/c mice yield inconsistent results with *C. pneumoniae* due to their stronger macrophage response. Other known *Chlamydia* species include *C. trachomatis, C. pecorum, C. muridarum*, and *C. suis*. One of skill will appreciate that various species and strains of *Chlamydia* and various mouse strains can be combined to provide a mouse model of the invention wherein infection of a particular mouse strain with a particular species and/or strain of *Chlamydia* will produce an infection with clear symptoms and/or effects without resulting in lethality that would hamper interpretation of results.

Further provided is a rational approach for selection of the challenge dose of *Chlamydia* spp. for the mouse strain selected in order to provide a functional mouse lung disease model. Disease severity and/or outcome may be assessed by measurement of any of various suitable parameters, such as, for example, the increase in lung weight, the amount of lung load of chlamydial organisms, or the level of NOS2 expression. Low-responder and high-responder mice have very different overall disease outcomes after inoculation with *Chlamydia psittaci*. As shown in FIG. 1, low responder mice such as BALB/c show increased severity of disease with increasing challenge inoculation, while high responder C57BL/6J mice show disproportionately severe disease at low inocula, peak disease development in the middle range of inocula, and low disease at high inocula. One of skill will appreciate that the degree of disease severity may be assessed by measurement of any suitable parameter.

Disease severity in the test mouse or mouse population may differ from disease severity in the reference mouse or mouse population by any measurable amount. Thus, disease severity as measured by at least one parameter may differ by at least 5%, 10%, 15%, 20%, 25,%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, 500%, 550%, 600%, 650%, 700%, 750%, 800%, or more percent. Disease severity may differ by at least 10-fold, 15-fold, 20-fold, 25-fold, or 30-fold or more as measured by at least one parameter.

While the invention is not bound by a particular mechanism, it is believed that the phenomenon of low disease at high inocula exhibited by C57BL/J mice results from an effective containment of chlamydial replication by the high macrophage response combined with strong stimulation of the adaptive immune response during which apoptosis is induced to a lesser degree than at low antigen stimulation. Thus, a high macrophage response is beneficial at very high chlamydial inocula but enhances disease at low chlamydial inocula. One of skill will be able to determine a specific inoculum or dose of *Chlamydia* for which a low responder mouse previously not exposed to *Chlamydia* develops pronounced but generally non-lethal disease. In providing the development of pronounced but generally non-lethal disease, such a combination of mouse and *Chlamydia* inoculum or dose provides a functional mouse model of the invention.

Mice of the same strain previously exposed to a low dose of *Chlamydia* (1/100 of challenge inoculum) or appropriately immunized with an effective vaccine will show much lower disease severity (as measured, for example, by chlamydial lung burden) between 7–12 days after challenge inoculation. Thus, one of skill will appreciate that an optimum inoculum dose or range of doses can be identified that maximizes the difference in disease outcomes for naïve mice versus protected mice. Such an optimum inoculum dose or range of doses allows evaluation of the prophylactic or protective effect conferred, for example, by vaccination or other treatment. *Chlamydia* may be administered to mice by any suitable means, such as, for example, intranasal means, intraocular means, or by injection or orally, etc.

Thus, for example, as demonstrated by the results shown in FIG. 1, the optimum inoculum of *C. psittaci* in C57BL/6 mice can be between $1 \times 10^4$ IFU and $1 \times 10^7$ IFU or between $9 \times 10^4$ IFU and $5 \times 10^6$ IFU or between $2 \times 10^5$ IFU and $3 \times 10^6$ IFU. The optimum inoculum may vary depending on the procedures used in preparation for and in conducting such experiments or tests, as one of skill will recognize. Thus, the optimum inoculum could be essentially about $1 \times 10^2$ IFU, $2 \times 10^2$ IFU, $5 \times 10^2$ IFU, $7 \times 10^2$ IFU, $1 \times 10^3$ IFU, $2 \times 10^3$ IFU, $5 \times 10^3$ IFU, $7 \times 10^3$ IFU, $1 \times 10^4$ IFU, $2 \times 10^4$ IFU, $4 \times 10^4$ IFU, $6 \times 10^4$ IFU, $8 \times 10^4$ IFU, $1 \times 10^5$ IFU, $2 \times 10^5$ IFU, $4 \times 10^5$ IFU, $6 \times 10^5$ IFU, $8 \times 10^5$ IFU, $1 \times 10^6$ IFU, $2 \times 10^6$ IFU, $4 \times 10^6$ IFU, $6 \times 10^6$ IFU, $8 \times 10^6$ IFU, $1 \times 10^7$ IFU, $2 \times 10^7$ IFU, $5 \times 10^7$ IFU, $7 \times 10^7$ IFU, $1 \times 108$ IFU, $2 \times 10^8$ IFU, $5 \times 10^8$ IFU, $7 \times 10^8$ IFU, $1 \times 10^9$ IFU, $2 \times 10^9$ IFU, $5 \times 10^9$ IFU, or $7 \times 10^9$ IFU. It will be understood that the optimum inoculum could be a range of values with a lower endpoint and a higher endpoint selected from the preceding list. For example, the optimum inoculum could be a dose consisting of $2 \times 10^5$ IFU–$8 \times 10^5$ IFU. As discussed above, one of skill will be able to determine a specific inoculum or dose of *Chlamydia* for the particular combination of interest of mouse and *Chlamydia* which results in the development by the mouse of pronounced but generally non-lethal disease. In providing the development of pronounced but generally non-lethal disease, such a combination of mouse and *Chlamydia* inoculum or dose provides a functional mouse model of the invention.

IFUs (inclusion forming units) as a measure for chlamydial inoculum or infectivity is determined by cell culture inoculation and subsequent determination of the number of inclusions. Because it is a biological assay, it is subject to some variability depending on procedural details including the person who is actually counting the number of inclusions.

Another measurement of inoculum or infectivity is *Chlamydia* genomes, which are typically counted after extensive sonication to disrupt clumps and produce a single-organism suspension. The optimum inoculum of *Chlamydia* genomes into mice can be between $1 \times 10^4$ genomes and $1 \times 10^7$ genomes or between $9 \times 10^4$ genomes and $5 \times 10^6$ genomes or between $2 \times 10^5$ genomes and $3 \times 10^6$ genomes. The optimum inoculum may vary depending on the procedures used in preparation for and in conducting such experiments or tests, as one of skill will recognize. Thus, the optimum inoculum could be essentially about $1 \times 10^2$ genomes, $2 \times 10^2$ genomes, $5 \times 10^2$ genomes, $7 \times 10^2$ genomes, $1 \times 10^3$ genomes, $2 \times 10^3$ genomes, $5 \times 10^3$ genomes, $7 \times 10^3$ genomes, $1 \times 10^4$ genomes, $2 \times 10^4$ genomes, $4 \times 10^4$ genomes, $6 \times 10^4$ genomes, $8 \times 10^4$ genomes, $1 \times 10^5$ genomes, $2 \times 10^5$ genomes, $4 \times 10^5$ genomes, $6 \times 10^5$ genomes, $8 \times 10^5$ genomes, $1 \times 10^6$ genomes, $2 \times 10^6$ genomes, $4 \times 10^6$ genomes, 6 genomes, $8 \times 10^6$ genomes, $1 \times 10^7$ genomes, $2 \times 10^7$ genomes, $5 \times 10^7$ genomes, $7 \times 10^7$ genomes, $1 \times 10^8$ genomes, $2 \times 10^8$ genomes, $5 \times 10^8$ genomes, $7 \times 10^8$ genomes, $1 \times 10^9$ genomes, $2 \times 10^9$ genomes, $5 \times 10^9$ genomes, or $7 \times 10^9$ genomes. It will be understood that the optimum inoculum could be a range of values with a lower endpoint and a higher endpoint selected from the preceding list. For example, the optimum inoculum could be a dose consisting of $2 \times 10^5$ genomes –$8 \times 10^5$ genomes. As discussed above, one of skill will be able to determine a specific inoculum or dose of *Chlamydia* for the particular combination of interest of mouse and *Chlamydia* which results in the development by the mouse of pronounced but generally non-lethal disease. In providing the development of pronounced but generally non-lethal disease, such a combination of mouse and *Chlamydia* inoculum or dose provides a functional mouse model of the invention.

In some embodiments of the invention, the combination of mouse and *Chlamydia* will result in rapid lethality and/or a high degrees of lethality in an inoculated test mouse population. In these embodiments, the effectiveness of a prophylactic or therapeutic treatment may be assessed by an increased time to lethality or a lower level of lethality in the test mouse population when compared to a reference mouse population. A lower level of lethality can also be measured by assessment of the $LD_{50}$ for a selected treatment, e.g., a particular strain and inoculum of *Chlamydia*. Methods for determining the $LD_{50}$ for a selected treatment are known in the art. Typically, such methods involve inoculation of mice with inocula that are increased logarithmically, calculating the percentage of dead mice for each inoculum, and then calculating a best fit curve to determine the inoculum that corresponds to 50% lethality.

Further provided is a rational approach for selecting the composition of mouse diets used during challenge experiments. Because chlamydial disease outcome is affected by the enzymatic production of NO, chlamydial disease can be affected by factors that influence levels of substrate for nitric oxide synthase-2 (NOS2), the major immune-associated NO-producing enzyme. NO acts as a non-redundant intracellular messenger molecule which is required in multiple physiological processes, including regulation of the immune response. Thus, while a high production of NO is undesirable for the best protection against chlamydial disease, too little NO is also detrimental. The substrate of NOS2 is the amino acid arginine, which is a component of proteins and also is a substrate in the urea cycle for excretion of nitrogen. While homeostasis of arginine is tightly regulated, the steady-state equilibrium levels of arginine are largely dependent on arginine and protein levels in the diet. Thus, arginine and protein content of the diet can influence the outcome of chlamydial disease. Experiments described in Example 2 show that in order to maximally enable the immune response, it may be necessary to feed a high protein-arginine diet during challenge or inoculation with *Chlamydia*.

Thus, for example, as shown by the results discussed in Example 2, the protein content of the diet to be fed to the selected mouse and/or mouse strain could include about 7%, 8%, 9% or 10% protein, about 11%, 12%, 13%, 14%, 15%, 16%, 17%, 18%, 19%, 20%, 21%, 22%, 23%, 24%, 25%, 26%, 27%, 28%, 29%, 30%, or a higher percentage of protein. Thus, it will be understood that the selected protein content of the diet could be a range of values with a lower endpoint and a higher endpoint selected from the preceding list. For example, the optimum protein content of the diet could be a percentage of protein between 10% and 30%, or between 15% and 20%. The arginine content of the diet to be fed to the selected mouse and/or mouse strain could include about 0.1% arginine, about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.5%, 3.0%, 3.2%, 3.5%, 4.0%, or higher amounts of arginine. Thus, it will be understood that the selected arginine content of the diet could be a range of values with a lower endpoint and a higher endpoint selected from the preceding list. For example, the selected arginine content could be between 0.5% and 1.4%.

The methods and compositions of the invention find use in evaluating therapeutic and prophylactic treatments for *Chlamydia* infection. One of skill in the art will appreciate that the order of steps in the method may vary depending on the treatment being evaluated. Thus, if the treatment is prophylactic, the treatment will typically be administered to the mouse prior to the administration of the test inoculation or dose of *Chlamydia*. Similarly, if the treatment is therapeutic, the treatment will typically be administered to the mouse after administration of the test inoculation of *Chlamydia*. Similarly, the order of the steps of selecting a mouse strain, selecting a dose of *Chlamydia*, and selecting a feeding regimen is not important so long as the object of the invention is accomplished; that is, so long as the method permits evaluation of the efficacy of a therapeutic or prophylactic treatment of *Chlamydia*-induced disease. A prophylactic or therapeutic treatment may be any drug, food, regime of treatment, etc. which is being tested for its efficacy in reducing the severity, impact, etc. of chlamydial disease.

One of skill is able to select a suitable combination of mouse and *Chlamydia* species, strain, and/or dose to produce a mouse model that will permit evaluation of *Chlamydia*-induced disease. The selection of mouse and *Chlamydia* necessarily involves some routine experimentation to optimize the combination of these various aspects. See, for example, Hau et al., eds. (2002) *Handbook of Laboratory Animal Science, Second Edition: Essential Principles and Practices,* Vols. I and II (CRC Press, Boca Raton, Fla.). However, such experimentation is well within the skill of those in the art and is also illustrated in the working examples provided herein.

It will be appreciated by those of skill in the art that while the working examples presented herein relate to *Chlamydia* infection, the principles used to generate a mouse model as described herein are more generally applicable for studying the immune response as it is affected by any genetic and/or environmental factor.

Severity of chlamydial disease can be assessed in a variety of ways. As described in the working examples, severity of disease can be assessed, for example, by measuring morbidity and/or lethality or mortality, by measuring increase in lung weight, by measuring total chlamydial lung burden using, for example, fluorescence resonance energy transfer quantitative PCR ("FRET-qPCR"), by measuring transcript and/or enzyme levels in macrophages, by monitoring the production of NO, etc. Further, as illustrated in the working examples provided herein, disease severity can be assessed, for example, by measuring DTH, by assaying antibodies against *Chlamydia*, and/or by examining tissue such as lung tissue. One of skill will measure at least one parameter of disease severity suitable for the particular assay performed. One of skill will also assess disease severity at a particular point in time that is selected to allow distinction between experimental (treated) and control animals. Thus, disease severity may be assessed at about several hours to one day after inoculation or at 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, or more days after inoculation.

As shown by the working examples provided herein, a quantitative examination of *Chlamydia*-induced interstitial pneumonia showed that C57BL/6 mice were highly prone to severe disease after intranasal inoculation with moderate doses of chlamydiae but were protected from disease after high-dose inoculation. The C57BL/6 low-dose susceptibility was first evident 1 week after inoculation of naïve animals, at a time when the nascent adaptive immune response typically redirects innate defense mechanisms. Measurements of DTH, antibody production, and splenocyte proliferation indicated that the adaptive immune response was strongly suppressed in C57BL/6 mice and was moderately Th2-biased at peak disease. BALB/c mice exhibited a reversed phenotype of disease susceptibility. This protection of BALB/c from disease susceptibility was associated with high DTH and IgG2a antichlamydial immunity, consistent with a Th1 adaptive immune response and with the absolute requirement of MHC 11-restricted IFN-γ release for clearance of chlamydial infection (see Huang et al. (1999) *J. Immunol.* 162: 2217–2226; Igietseme et al. (1993) *Reg. Immunol.* 5: 317–324; Morrison et al. (1995) *Infect. Immun.* 63: 4661–4668; Rank (1999) in *Chlamydia*, ed. Stephens, R. S. (Am. Soc. Microbiol., Washington, D.C.), pp. 239–295; Rottenberg et al. (1999) *J. Immunol.* 162: 2829–2836; Holland et al. (1993) *J. Infect. Dis.* 168: 1528–1531). The suppressed adaptive immunity to chlamydiae observed in C57BL/6 mice is reminiscent of the scarring trachoma caused by chronic *C. trachomatis* infection in human patients. In trachoma patients, peripheral blood mononuclear cells yield significantly reduced lymphoproliferative responses to chlamydial antigens compared with asymptomatic, *C. trachomatis*-infected individuals (see Holland et al. (1993) *J. Infect. Dis.* 168: 1528–1531).

While the invention is not bound by any particular mechanism of operation, the reversal of susceptibility to Chlamydia-induced disease suggests that in early Chlamydia infection the IL-12-IFN-γ signaling circuitry between macrophages, natural killer (NK) cells, and activated Th1 cells maintains high levels of both protective cytokines only within a narrowly restricted range of NO release. In the absence of NO, IL-12 signaling in NK cells is blocked, thus reducing the IFN-γ release of NK cells (see Diefenbach et al. (1999) *Science* 284: 951–955) and rendering the innate defense ineffective against chlamydial infection. Too low a level of NO production may also explain the increased severity of secondary *C. psittaci* disease in BALB/c mice treated with a high dose of AG (FIG. 3, panel C). Conversely, high macrophage NO release, driven by NK and CD4 T cell-derived IFN-γ, is known to induce immunosuppression (see Schwacha and Eisenstein (1997) *Infect. Immun.* 65: 4897–4903; Schwacha et al. (1998) *Infect. Immun.* 66: 5862–5866). High macrophage NO release also is known to down-regulate Th1 cell development by inhibition of macrophage IL-12 synthesis (see Huang et al. (1998) *Eur. J. Immunol.* 28: 4062–4070) and selective induction of apoptosis of activated Th1 cells (see Dalton et al. (2000) *J. Exp. Med.* 192: 117–122). Consistent with this concept are the significantly enhanced lung levels of IL-12 and IFN-γ as well as the day-4 increase in splenic CD4 T cells of *C. psittaci*-infected C57BL/6 mice protected by 6 mg/kg AG to the level of BALB/c. While the invention is not bound by any particular mechanism of action, collectively, these data indicate that activated CD4 T cells secreting IFN-γ indirectly trigger their own apoptosis when they activate macrophages of high NO responders but that they proliferate in the presence of low NO responder macrophages (see Dalton et al. (2000) *J. Exp. Med.* 192: 117–122). Thus, the decisive factor in development of chlamydial disease may be a high rate of increase in macrophage NO production in response to increasing quantities of chlamydial and host inflammatory stimuli.

NOS2-synthesized NO is important in human immune regulation and disease (see Allione et al. (1999) *J. Immunol.* 163: 4182–4191), although high levels of NO are not found in supernatants of cultured human macrophages (see Gantt et al. (2001) *J. Immunol.* 167: 893–901), and intracellular L-arginine concentration is elevated during high NO production in human airway epithelium (see Guo et al. (2000) *J. Immunol.* 164: 5970–5980). The results discussed herein show that macrophage NO production in inbred mice is at least partially genetically determined. This genetic component of macrophage response in mice suggests that similar high and low NO responder genotypes with differential susceptibility to chlamydial disease may exist in the human population.

Different responder genotypes are potentially important in the context of atherosclerosis and coronary heart disease in humans. *C. pneumoniae* is found in high frequency in atherosclerotic lesions (see Jackson et al. (1997) *Am. J. Pathol.* 150: 1785–1790), and NOS2 enhances atherosclerosis in mouse models (see Detmers et al. (2000) *J. Immunol.* 165: 3430–3435). Whereas infectious agents are not required for initiation or progression of atherosclerosis (see Wright et al. (2000) *J. Exp. Med.* 191: 1437–1441), the presence of *C. pneumoniae* in murine atherosclerotic lesions increases lesion size and disease progression (see Moazed et al. (1999) *J. Infect. Dis.* 180: 238–241; Hu et al. (1999) *J. Clin. Invest.* 103: 747–753). Thus, repeated *C. pneumoniae* infection of high NO responding individuals might precipitate a vicious cycle of exacerbated and prolonged proatherogenic inflammatory responses (see Ross (1999) *N. Eng. J. Med.* 340: 115–126). Such inflammatory responses would have the potential to greatly accelerate an otherwise slow progression toward coronary atherosclerosis.

Because of these inflammatory responses, vaccination of high NO responding individuals to provide immunoprotection from chlamydial disease might pose a risk to their health. The model presented herein provides a collection of parameters which could also be considered in vaccination of humans against *Chlamydia*. Consideration of these parameters could make prevention and control of human chlamydial disease more predictable and reliable processes. Without reduction of macrophage NO release during enhanced vaccine-mediated T-cell responsiveness by pharmacological or other means, only genetic triage of high NO-responding individuals from a vaccinee population might ensure minimal undesirable side effects of vaccination against *Chlamydia*.

EXPERIMENTAL

We had previously found that the susceptibility of BALB/c and C57BL/6 inbred mouse strains to chlamydial disease differed widely in a model of lung infection with a virulent ruminant abortifacient strain of *Chlamydia psittaci*. See Kaltenboeck et al. (1998) in *Chlamydial Infections: Proceedings of the Ninth International Symposium in Human Chlamydial Infection, Napa, Calif., June* 1998, ed. Stephens, R. S. (Univ. of California Press, Berkeley), pp. 403–406. At the peak of the early inflammatory response on days 3–5 after intranasal inoculation of high doses of *C. psittaci* (0.5–1×$10^7$ inclusion-forming units (IFU)), naïve C57BL/6 mice appeared healthy whereas BALB/c mice showed clinical signs of disease, including ruffled fur and labored respiration. C57BL/6 mice also had a higher $LD_{50}$ than BALB/c mice for the 12-day period after infection. See Kaltenboeck et al. (1998), id.

We attributed these effects to differences in the innate immune response. However, in repeated lung infection, C57BL/6 mice primed by low-level intranasal infection developed severe interstitial pneumonia after secondary challenge whereas BALB/c mice were completely protected from clinical disease. See Kaltenboeck et al. (1998), id. The lung disease in C57BL/6 mice exhibited extensive interstitial infiltrates of macrophages, lymphocytes, and neutrophils, features which are characteristic of chlamydial disease (see Schachter, J. (1999) in *Chlamydia*, ed. Stephens, R. S. (Am. Soc. Microbiol., Washington, D.C.), pp. 139–169). This infiltration resulted in profound lung weight increases over those of naïve controls. Resistant BALB/c mice had prominent peribronchiolar lymphocytic cuffs but minimal lung weight increases (see Kaltenboeck et al. (1998), id.).

We continued to study this dichotomy of the disease response using clinically more relevant, nonlethal chlamydial inocula. While the invention is not bound by any particular mechanism of action, we found that differences in NO release by infected macrophages are responsible for the differential susceptibility of C57BL/6 and BALB/c mice to primary and repeated chlamydial disease. Elevated NO synthesis in C57BL/6 mice provides protection against high-dose infection with virulent chlamydiae, but suppresses adaptive immunity at more moderate infection. This results in reduced elimination of chlamydiae at moderate infection, precipitates development of increased interstitial pneumonia, and delays resolution of the pneumonia in disease-susceptible C57BL/6 mice compared with resistant BALB/c mice. This role of NO in regulating chlamydial disease reinforces the double-edged nature of this molecule with the potential for beneficial as well as deleterious effects (see MacMicking et al. (1997) *Annu. Rev. Immunol.* 15: 323–350) and also indicates that both too much and too little NO can have negative effects on protective immunity.

Example 1

C57BL/6 Mouse Model of *Chlamydia*-Induced Disease Materials and Methods

Chlamydial Lung Infection. *C. psittaci* strain B577 (ATCC strain VR-656) and *C. pneumoniae* strain CDC/CWL-029 (ATCC strain VR-1310) were grown and purified as described in Huang et al. (1999) *J. Immunol.* 162: 2217–2226. Six-week-old to eight-week-old female mice were fed rodent chow containing 19.9% protein (weight/weight) and 1.33% (w/w) L-arginine (Harlan Teklad LM-485). Mouse strains used were obtained from Harlan Sprague-Dawley, except for the NO synthase 2 (NOS2) –/– mice, which were strain B6;129P2-Nos2$^{tm1Lau}$ (stock number 002956) obtained from The Jackson Laboratory, Bar Harbor, Me. (see Laubach et al. (1995) *Proc. Nat'l. Acad. Sci. USA* 92: 10688–10692) and C57BL/6 control mice (NOS2$^{+/+}$, from The Jackson Laboratory). Drinking water (pH 2.5) with L-norvaline (Sigma) was prepared freshly every other day. Average daily consumption was 2.7 ml drinking water for BALB/c mice and 3.2 ml for C57BL/6 mice. Aminoguanidine (AG)-treated mice received two intraperitoneal injections per day of 0.2 ml PBS-AG hemisulfate (Sigma).

Mice were inoculated intranasally as described in Huang et al. (1999) *J. Immunol.* 162: 2217–2226. At high-dose inoculation, some BALB/c mice developed lethal disease after seven days. Moribund mice were killed before termination of the experiment on day 12 to obtain unbiased results. Lungs or macrophages were suspended (10% wt/vol) in guanidium isothiocyanate-Triton X-100-based RNA/DNA stabilization reagent (Roche Molecular Biochemicals). DNA was extracted by glass filter absorption (Roche Molecular Biochemicals), mRNA with biotin-oligo (dT), and streptavidin magnetic beads (Roche Molecular Biochemicals). Data were analyzed by two-tailed Student's t test.

Immune parameters. Chlamydial elementary bodies were lysed by boiling in 0.065 M Tris-HCl (pH 7.0), 0.17 M DTT, 2% SDS, and 10% glycerol and washed by 5× ultrafiltration (Microcon YM-3, Millipore) in PBS-20 mM DTT. Twenty-four hours after footpad injection of 25 μl antigen solution containing 0.5 μg chlamydial protein, delayed type hypersensitivity (DTH) was determined by measuring the increase in footpad thickness with a spring-equipped dial thickness gauge (Huang et al. (1999) *J. Immunol.* 162: 2217–2226). For antibody ELISA, chlamydial lysate (0.4 μg protein/well) was coated onto white microtiter plates, and antibodies in 1:100 diluted sera were detected with biotinylated anti-mouse IgG1 or IgG2a goat antiserum (Southern Biotechnology Associates) and streptavidin-peroxidase and luminol chemiluminescent substrate (Kirkegaard & Perry Laboratories).

Total splenic CD4$^+$ T cells of mice on day 4 after infection with 8.1×10$^5$ inclusion-forming units (IFU) *C. psittaci* were determined by flow cytometry with FITC anti-mouse CD4 and phycoerythrin-anti-mouse CD3 (PharMingen). Total splenocytes were cultured in RPMI 1640 medium with 10% FBS (Life Technologies, Grand Island, N.Y.) and 5 μg ovalbumin or chlamydial lysate protein/ml in white flat-bottom 96-well cell culture plates. Cells were pulsed with BrdUrd and permeabilized (Roche Molecular Biochemicals), and BrdUrd incorporated into DNA was detected by anti-BrdU-peroxidase and luminol.

Thioglycolate-elicited peritoneal phagocytes were incubated at $10^6$ cells/ml/well in 24-well tissue culture plates in RPMI 1640 medium containing 50 μM L-arginine and 10% FBS. Adherent macrophages were infected with $10^7$ IFU *C. psittaci*/ml and lysed in situ in RNA/DNA stabilization reagent, and mRNA was extracted.

Cumulative NO production was determined by the Griess reaction (R&D Systems) as total serum nitrite concentration.

Quantitative PCR (qPCR). *C. psittaci* B577 fluorescence resonance energy transfer (FRET)-qPCR was performed as described in Huang et al. (2001) *BioTechniques* 30: 150–157. In the FRET-qPCR for *C. pneumoniae*, the *C. psittaci* B577 probe was replaced by the *C. pneumoniae*-specific probe 5'-CACATTAAGTTCTTCAACTTTAGGTTT -fluorescein-3'(SEQ ID NO:1).

For real-time reverse transcription (RT)-qPCR oligo(dT)-primed mRNA was reverse-transcribed with Thermoscript reverse transcriptase (Life Technologies). RT reactions were diluted to 80 μd with 10mM TrisHCl (pH 8.5), 0.1 mM EDTA ($T_{10}E_{0.1}$) and 5 μl aliquots were used for qPCR (Huang et al. (2001) *BioTechniques* 30: 150–157). Thermal cycling was performed in a LightCycler (Roche Molecular Biochemicals) for 0 s at 95° C. and 6 s at 70° C. SYBR green fluorescence was acquired after 10 s equilibration at 84–86° C., approximately 1–2° C. below the $T_m$ of the respective amplicon. Mouse-specific primers were used at 1μM: β-actin, sense: 5'-CTCCTCCTGAGCGCAAGTACTCTGTGT-3'(SEQ ID NO:2); β-actin, antisense: 5'-GTGCACGATGGAGGGGCCGGACTCAT-3'(SEQ ID NO:3); NOS2, sense, 5'-CACTTGGATCAGGAACCTGAAGCCC-3'(SEQ ID NO:4); NOS2, antisense, 5'-CTTTGTGCTGGGAGTCATGGAGCCG-3'(SEQ ID NO:5); arginase I, sense, 5'-AGCTGGGGATTGGCAAGGTGATGGA-3'(SEQ ID NO:6); arginase I, antisense, 5'-AGCCCTGTCTTGTAAATTTCTTCTGTGA-3'(SEQ ID NO:7); arginase II, sense, 5'-CTGTAGCTATAGTCGGAGCCCCTTTCT-3' (SEQ ID) NO:8); and arginase II, antisense, 5'-GTGGCATCCCAACCTGGAGAGC-3'(SEQ ID NO:9).

Standard templates were prepared by agarose gel purification of PCR fragments amplified with deoxythymidine 5'-triphosphate (dTTP) instead of dUTP. TTP amplicons were confirmed by automated DNA sequencing, quantified by PicoGreen fluorescence (Molecular Probes, and diluted in $T_{10}E_{0.1}$ containing 5 μg/ml sheared plasmid (pGEM) DNA.

A FRET RT-qPCR for detection of polymorphisms at position 3083 of the murine NOS2 locus used NOS2 primers and reagents described above. Probes were used at 0.5 μM: NOS 2 downstream 5'-(LightCycler Red 640)-CATCCTCATTGGGCCTGGTACG-(phosphate)-3'(SEQ ID NO:10); NOS2 upstream 5'-TGAGGACCCCTTCCAGCCTT-(FLUORESCEIN)- 3'(SEQ ID NO:11). Thermal cycling parameters were 0 seconds (s) at 95° C., 3 s at 59° C. followed by fluorescence acquisition, and 10 s at 72° C.

Results.

Differential Susceptibility of BALB/c and C57BL/6 Mice to *Chlamydia*-Induced Disease. In order to reflect the typical chronic and nonlethal human chlamydial disease (see Schachter, J. (1999) in *Chlamydia*, ed. Stephens, R. S. (Am. Soc. Microbiol., Washington, D.C.), pp. 139–169), we evaluated the time course of induction of lung disease following a moderate intranasal inoculum ($8.1\times10^5$ IFU of *C. psittaci*) in BALB/c and C57BL/6 mice. As indicated in FIG. 1, mice were sacrificed at 4 days after inoculation as well as 7 days, 12 days, 20 days, and 28 days after inoculation. At the time of maximum lung disease on day 12, C57BL/6 mice had more than two times the lung weight increase of BALB/c mice (FIG. 1, panel A), thus reversing the pattern of disease resistance exhibited at high inocula. Lungs of C57BL/6 mice had severe interstitial pneumonia with extensive mononuclear inflammatory cell infiltrates and large areas of lung consolidation, whereas those of BALB/c mice appeared grossly and microscopically normal with only a few small foci of peribronchiolar mononuclear cell infiltrates. The more severe disease in C57BL/6 mice was accompanied by significantly elevated total chlamydial lung burden, reduced elimination of chlamydiae, and poor resolution of interstitial pneumonia (FIG. 1, panels A and B). One of skill will appreciate that even an inbred mouse population exposed to the same environment will show some variation in their response to factors of interest. Nevertheless, the effects of the factors of interest (e.g., inoculation with bacteria) can be evaluated using appropriate statistical techniques where necessary.

The differential susceptibility of these mouse strains to *Chlamydia*-induced interstitial pneumonia corresponded to highly significant differences in delayed-type hypersensitivity (DTH) and antibody responses to *C. psittaci* antigens (FIG. 1, panels C-E). C57BL/6 mice had significantly lower DTH and IgG2a responses at all time points compared with BALB/c mice, but a higher IgG1 response on day 12 (FIG. 1, panel D). On day 12, the proliferation index of infected C57BL/6 splenocytes stimulated with *C. psittaci* antigen was 5.7-fold (±0.4; SEM) greater than that of splenocytes stimulated with ovalbumin, whereas the index of BALB/c splenocytes was 17.0-fold greater (±2.1; n=8/group; $P_{C57BL/6:BALB/c}$=0.0003). Thus, BALB/c mice developed vigorous immunity against *Chlamydia* and rapidly eliminated organisms and disease, whereas C57BL/6 mice showed suppressed immunity and exacerbated disease.

Next, we examined the patterns of day-12 disease induced by a wide range of *C. psittaci* dose levels. At low intranasal doses (0.3–8.1×$10^5$ IFU *C. psittaci*), C57BL/6 mice again developed substantially more severe disease and higher chlamydial lung burden than BALB/c mice (FIG. 1, panels G and H). At higher doses, which approached the BALB/c day-12 $LD_{50}$ (4×$10^6$ IFU *C. psittaci*), C57BL/6 mice developed less severe disease than BALB/c mice. Still higher infection doses of $10^7$ IFU or greater typically resulted in early death of many C57BL/6 mice between days 3 and 6 from acute pulmonic shock, whereas BALB/c mice succumbed to interstitial pneumonia between days 7 and 11. Serum IgG2a concentrations in C57BL/6 mice averaged 10% of those in BALB/c mice (FIG. 1, panel K), whereas day-12 IgG1 concentrations were marginally higher than those of BALB/c mice (FIG. 1, panel J). The DTH response of BALB/c mice infected with the highest dose declined below that of corresponding C57BL/6 mice (FIG. 1, panel I). These results confirmed the dichotomy of C57BL/6 disease susceptibility, with resistance at high dose and susceptibility at clinically relevant, low-dose chlamydial infection, and a reversed susceptibility pattern in BALB/c mice.

Analysis of NO Production. We evaluated total serum nitrite/nitrate as an indicator of cumulative NO production. Macrophage-released NO synthesized by NOS2, the high output NOS isoenzyme, acts as a regulator of lymphocyte growth and is immunosuppressive through the induction of apoptosis in activated T cells (see Eisenstein et al. (1994) *Immunobiology* 191: 493–502). C57BL/6 mice produced significantly more NO than BALB/c mice at all time points after infection (FIG. 1, panel F). When the early innate NO response to a range of chlamydial doses was tested, the magnitude of NO output correlated with increasing chlamydial doses in C57BL/6 mice whereas BALB/c mice showed little change in NO output (FIG. 1. panel L).

NOS2 expression in *Chlamydia*-infected lung tissue was examined by immunohistochemical staining (see FIG. 4). Lesions in infected lungs were either double-stained (cryosections) or single-stained as serial sections (formalin-fixed sections) with antibodies against *C. psittaci*, NOS2, or the macrophage maturation marker F4/80. These experiments revealed that NOS2 was virtually exclusively expressed in both mouse strains by F4/80-positive lung macrophages, which were also the main target cells for chlamydial infection (FIG. 4). *C. pneumoniae* has also been shown to principally target macrophages (see Moazed et al. (1998) *J. Infect. Dis.* 177: 1322–1325). However, infected macrophages of both mouse strains stained with similar intensity for NOS2, so NOS2 protein levels in macrophages did not explain the differences in NO release in the two strains.

To obtain more precise data on NOS2 expression, we analyzed NOS2 mRNA levels in day-4 infected lung tissue by RT-qPCR. After high-dose chlamydial inoculation, C57BL/6 mice had significantly higher NOS2 transcript levels than BALB/c mice. However, at doses of *C. psittaci* of 8.1×$10^5$ IFU or less, NOS2 mRNA concentrations did not differ between BALB/c and C57BL/6 mice (FIG. 2, panel A). Thus, at clinically relevant chlamydial doses, C57BL/6:BALB/c differential macrophage NO release was not a result of different NOS2 enzyme levels.

Another possible explanation for the low NO production of BALB/c mice was a mutant NOS2 enzyme having impaired activity. The NOS2 genes of a number of inbred mouse lines have identical ORFs (see Lyons et al. (1992) *J. Biol. Chem.* 267: 6370–6374; Xie et al. (1992) *Science* 256: 225–228). However, the BALB/c ByJ mouse strain (GenBank accession no. AF0651920) is an exception. This NOS2 gene differs from others by a single nonsynonymous polymorphism at position 3083, which results in the replacement of a phenylalanine residue by a serine residue at a position close to the putative NADPH ribose binding site of the reductase domain of murine NOS2 (see Lyons et al. (1992) and Xie et al. (1992), id.). We amplified a DNA fragment containing the polymorphic position from genomic DNA of several BALB/c and C57BL/6 mice and probed the amplicons with FRET probes in qPCR. No deviation from the consensus murine NOS2 sequence was observed. DNA sequencing also showed no mutation.

Because reduced NO production in BALB/c mice was not associated with reduced expression of NOS2 or a mutant NOS2, we considered differential regulation of substrate availability as the most likely mechanism of the differential NO output (see Mori and Gotoh (2000) in *Nitric Oxide*, ed. Ignarro, L. J. (Academic, New York), pp. 199–208). L-arginine is the substrate for NOS2 as well as for two arginase isoenzymes, cytosolic arginase I (GenBank accession no. U5810522) and extrahepatic mitochondrial arginase II (see Morris et al. (1998) *Am J. Physiol.* 275: E740-E747; Iyer et al. (1998) *Mol. Genet. Metab.* 63: 168–175). While the invention is not bound by any particular mechanism of operation, these two isoenzymes hydrolyze L-arginine to urea and ornithine and thus may reduce NO production by depleting the intracellular pool of L-arginine (Gotoh and Mori (1999) *J. Cell Biol.* 144: 427–434; Chang et al. (1998) *Am. J. Physiol.* 274: H342–H348). In vitro induction of either arginase isoenzyme in murine macrophages effectively down-regulates NO release and prevents NO-mediated apoptosis (Gotoh and Mori (1999) *J. Cell Biol.* 144: 427–434; Munder et al. (1999) *J. Immunol.* 163: 3771–3777).

Figure 2:
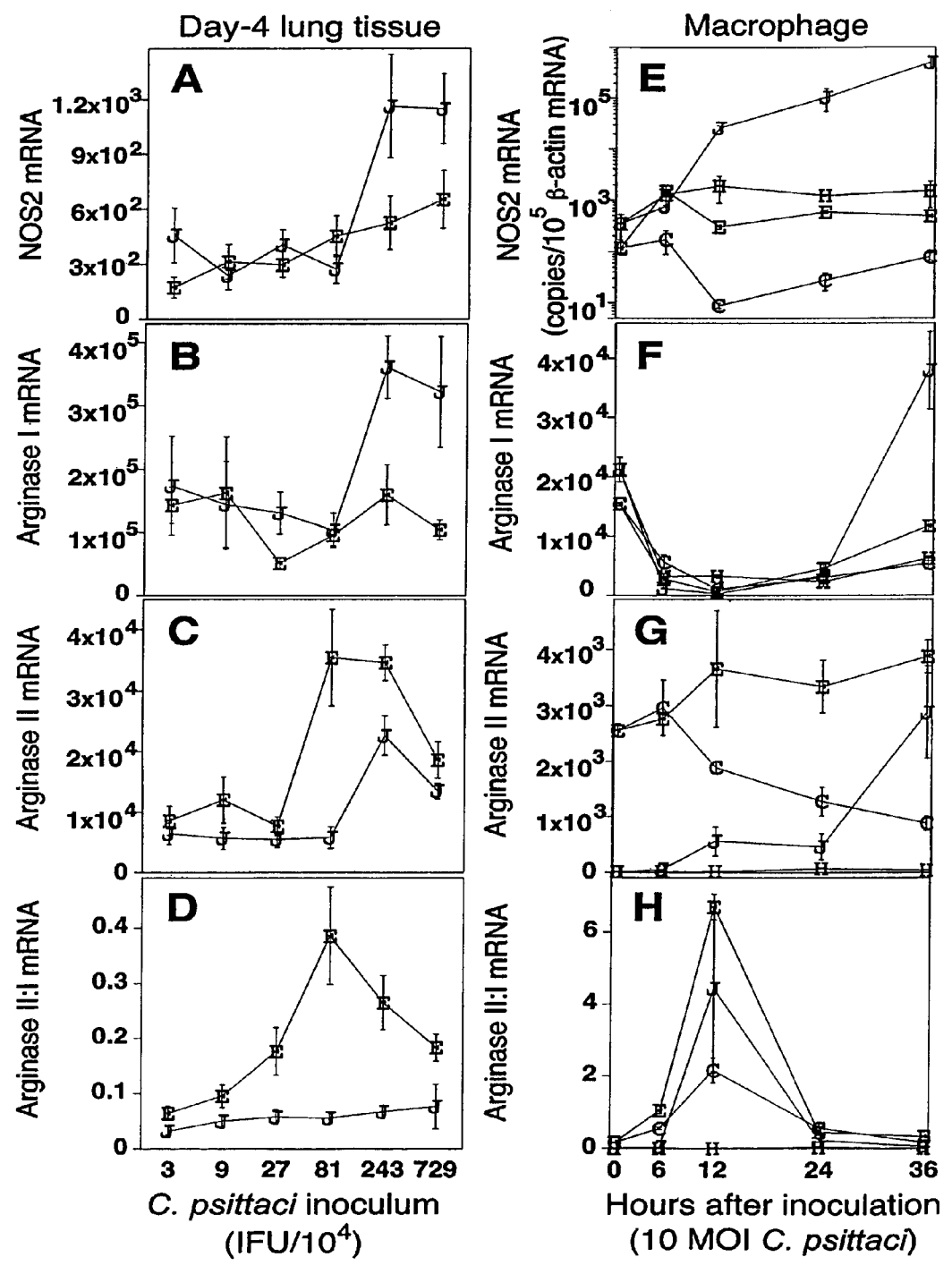

To determine whether differences in arginase expression were associated with the differential NO release in these mouse strains, we examined mRNA levels in infected lung tissue by RT-qPCR. A distinctive feature of BALB/c lung tissue exposed to low to intermediate doses of chlamydiae was an elevated level of arginase II transcripts, clearly visualized in the arginase II arginase I transcript ratio, which was significantly higher than in C57BL/6 mice (see FIG. 2). In contrast, the level of arginase I mRNA in BALB/c lungs did not differ significantly from that in C57BL/6 lungs (see FIG. 2, panels B–D). To examine whether the tissue levels of these transcripts reflected macrophage transcript levels, we tested the in vitro response of macrophages to chlamydial infection and found profound differences in macrophages from these mouse strains. Of the NOS2, arginase I, and arginase II genes, BALB/c macrophages selectively and highly transcribed only the arginase II gene immediately after stimulation (FIG. 2, panels E–H). In contrast, C57BL/6 macrophages responded more slowly, i.e., after 24 hours, but did so with sustained high levels of transcription, particularly of the NOS2 and arginase I genes.

These data are consistent with the low responsiveness reported for BALB/c macrophages to a variety of stimuli when compared with C57BL16 mice (see, e.g., Oswald et al. (1992) *J. Leukocyte Biol.* 52: 315–322). While the invention is not bound by any particular mechanism or model of operation, these data are also consistent with a preferential NOS2-mediated production of NO and citrulline by lipopolysaccharide/IFN-γ-stimulated C57BL/6 macrophages, and with a preferential arginase-mediated production of ornithine and urea by BALB/c macrophages, as reported by Mills et al. (2000) (*J. Immunol.* 164: 6166–6173) and proposed as a concept of M-1 and M-2 macrophages.

Reversal of Susceptibility Phenotype by Modulation of NOS2 Substrate Catalysis. We tested the role of L-arginine metabolism in NO production by treating infected mice with L-norvaline, a competitive inhibitor of arginase (Chang et al. (1998) *Am. J. Physiol.* 274: H342-H348; Tews and Harper (1986) *J. Nutr.* 116: 1464–1472). Treatment with L-norvaline was expected to increase intracellular L-arginine levels, and consequently NO production, of infected mice. At a dose of 1.5% L-norvaline in drinking water, but not at lower or higher doses, BALB/c mice produced more NO and partially reverted to a disease phenotype (FIG. 3, panel A).

We then tested whether a reversal of the C57BL/6 susceptible phenotype could be reversed by direct inhibition of the high-output NO-producing enzyme, NOS2. Mice were treated with AG, a selective, competitive inhibitor of NOS2 (see Corbett et al. (1992) *Diabetes* 41: 552–556). Intraperitoneal administration of AG reduced NO production of infected C57BL/6 mice in a dose-dependent manner. Six milligrams AG per kg body mass daily administered to naïve *C. psittaci*-infected mice completely protected C57BL/6 mice from disease and greatly reduced day-12 chlamydial lung burden (see FIG. 3, panel B). Other doses of AG did not change disease outcomes and numbers of chlamydiae in lung tissue. While the invention is not bound by any particular mechanism of operation, these results indicate that NO is a quantitative, nonredundant regulator of chlamydial disease.

We then tested the protective effect of NO reduction in a model of secondary lung disease. These tests were of interest because chlamydial disease typically results from numerous episodes of reinfection. Mice were intranasally primed with a low chlamydial inoculum and 5 weeks later were challenged with a second chlamydial inoculum, with and without administration of the NOS2 inhibitor AG. Results showed that daily administration of AG completely abolished the development of interstitial pneumonia in C57BL/6 mice on day 7 after secondary infection with *C. psittaci* (FIG. 3, panel C) or *C. pneumoniae* (FIG. 3, panel D). Treatment with AG reduced the chlamydial lung burden by up to more than 10-fold, although this required a higher dose of 100 mg per day (FIG. 3, panels C and D). These results demonstrate that macrophage NO regulates whether primary and repeated chlamydial infection results in disease. Intrinsically low NO-producing BALB/c mice remained unaffected by chlamydial challenge, while C57BL/6 mice were changed from a disease-susceptible to a completely resistant phenotype by the reduction, but not elimination, of NO production. Elimination of disease in C57BL/6 mice was consistently observed but required different levels of NOS2 inhibition depending on the level of chlamydial challenge and the specific immune status. These results indicate that NO is a quantitative, nonredundant regulator of chlamydial disease.

Optimum AG treatment level protects C57BL/6 mice. To better understand the complex, nonlinear mechanisms of disease protection resulting from reduced release of NO from macrophages, we studied the kinetics of *chlamydial pneumonia* under the influence of AG. C57BL/6 mice were treated with 6 mg AG/kg per day. These mice were protected from disease and resembled BALB/c mice in many aspects (see FIG. 5). When C57BL/6 mice were untreated or were treated with doses of AG that resulted in a high inhibition of NOS2 (i.e., 200 mg AG/kg per day), they developed severe disease that was closely parallel in each group.

This finding is consistent with our earlier experiment in which $NOS2^{+/+}$ and $NOS2^{-/-}$ C57BL/6 mice developed day-12 disease of similar severity after intranasal inoculation of $2.7\times10^5$ IFU *C. psittaci* ($NOS2^{+/+}$: 113.53±38% lung weight increase; $NOS2^{-/-}$: 100.49±31.3% lung weight increase). It is also consistent with results of others who did not observe differences in *C. trachomatis*-induced disease between $NOS2^{+/+}$ and $NOS2^{-/-}$ mice (see Perry et al. (1998) *Infect. Immun.* 66: 1265–1269; Igietseme et al. (1993) *Reg. Immun.* 66: 1282–1286; Ramsey et al. (2001) *Infect. Immun.* 69: 5131–5137). As demonstrated by the results shown in FIG. 3B, in high responder mice such as C57BL/6, only a very narrow zone of inhibition of NOS2 (here, from about 4 to about 15 mg AG) provides protection against the disease symptoms otherwise observed. Thus, mice treated with very high levels of AG show a similar disease phenotype to that exhibited by NOS2 knockout mice and also phenotypically resemble wild-type mice.

The most striking observation in C57BL/6 mice protected by 6 mg/kg AG was a significant increase in day-4 pulmonary concentrations of IL-12 p70 and IFN-γ transcripts (FIG. 5). These mice also showed a significant day-4 increase in splenic CD4 T cells to the level of BALB/c mice (BALB/c, 28.7% $CD4^+$ splenocytes ±1.33, n=6; C57BL/6, 23.2±0.05; C57BL/6+6 mg/kg per day AG, 28.0±0.55; $P_{C57BL/6:C57BL/6+6\ mg\ AG}$=0.005).

Thus, optimum AG treatment level protects C57BL/6 mice. While the invention is not bound by any particular mechanism of operation, AG treatment is thought to protect C57BL/6 mice by increasing early arginase II, IFN-γ, and IL-12p70 and reducing early arginase I expression.

In experiments to evaluate the effects of AG, mice were intranasally inoculated with $8.1\times10^5$ IFU *C. psittaci* (results shown in FIG. 5). C57BL/6 mice (solid circles) and BALB/c mice (open circles) were intraperitoneally injected with PBS. Other groups of C57BL/6 mice received AG daily at a dose of 6 mg/kg (solid diamonds) or 200 mg/kg (solid squares), and the time course of mRNA and IL-12p70 levels in lung tissue was determined (n =10, combined data of two experiments). Amplification of murine IFN- γ by qPCR followed the procedures described under Materials and Methods. Primers used were: 5'-TGCCAAGTTTGAGGT-CAACAACCCACAG-3'(IFN- γ, sense) (SEQ ID NO:12), and 5'-GCGACTCCTTTTCCGCTTCCTGAGG-3'(IFN- γ, antisense) (SEQ ID NO:13). For determination of IL-12p70, lungs were ground in 50 mM Tris-HCl, pH 7.5/10 mM EDTA, the suspension was clarified by low-speed centrifugation, and IL-12p70 in the supernatant was determined by ELISA (R&D Systems).

Panel A of FIG. 5 shows lung weight increase in mice treated under various regimes. C57BL/6 mice that were untreated or treated with 200 mg/kg AG developed severe day-12 disease, whereas BALB/c mice and C57BL/6 mice treated with 6 mg/kg AG were protected ($P_{C57BL/6:C57BL/6+6\ mgAG}$=0.017). Panel B of FIG. 5 shows total *C. psittaci* lung burden treated under these regimes. On day 4, untreated C57BL/6 mice had significantly lower chlamydial lung burdens than all other mice ($P_{C57BL/6:C57BL/6+6\ mg\ AG}$=0.007). On day 7, BALB/c and 200 mg/kg AG-treated C57BL/6 mice had higher chlamydial burdens than untreated and 6 mg/kg AG-treated C57BL/6 mice ($P_{C57BL/6:C57BL/6+200\ mgAG}$=0.077). After day 7, BALB/c and 6 mg/kg AG-treated C57BL/6 mice eliminated chlamydiae significantly more rapidly from lungs than untreated and 200 mg/kg AG-treated C57BL/6 mice ($P_{C57BL/6:C57BL/6+6\ mgAG}$=0.000001). Panel C shows the level of NOS2 transcripts in mice treated under these regimes. NOS2, arginase I, and arginase II transcript levels on days 4 and 12 in C57BL/6 mice treated with 6 mg/kg AG resembled those of BALB/c mice and were not significantly higher on day 7 than those of all other groups ($P_{C57BL/6:C57BL/6+6\ mgAG}$=0.54). C57BL/6 mice that were untreated and treated with 200 mg/kg AG had similar day-12 transcript levels that differed significantly from BALB/c mice and C57BL/6 mice treated with 6 mg/kg AG ($P_{C57BL/6:C57BL/6+6\ mgAG}$=0.037). Panel D of FIG. 5 shows IL-12p70 expression. On day 4, BALB/c mice and C57BL/6 mice treated with 6 mg/kg AG had significantly higher IL-12p70 and IFN-γ transcript lung levels than C57BL/6 mice that were untreated or treated with 200 mg/kg AG ($P_{C57BL/6:C57BL/6+6\ mgAG}$=0.0006). FIG. 5 panel E shows the level of arginase I transcripts; panel F shows the level of arginase II transcripts; panel G shows the ratio of arginase II to arginase I transcripts ($P_{day-4C57BL/6:C57BL/6+6\ mgAG}$=0.011); and panel H shows the level of IFN-γ transcripts ($P_{day4C57BL/6:C57BL/6+6\ mgAG}$=0.015).

Example 2

Analysis of Arginine/Protein Levels in Chlamydial Disease

We analyzed the influence of arginine/protein levels on disease outcome in an intranasal challenge model of A/J mice with *Chlamydia pneumoniae*. First, naïve female 6-week old A/J mice were fed one of an array of diets containing particular amounts of protein and arginine. These diets contained: 1) 12% protein, 0.5% arginine; 2) 14% protein, 0.7% arginine; 3) 16% protein, 0.9% arginine; 4) 18% protein, 1.1% arginine; or 5) 20% protein, 1.3% arginine. The mice were challenged with an inoculum of $3.5\times10^8$ *Chlamydia pneumoniae* and sacrificed after 7 days. Lung weights were determined, and disease severity was expressed as percent lung weight increase over those of mock-inoculated controls (Table 1).

TABLE 1

Day-7 disease in 6-week old female A/J mice inoculated with $3.5 \times 10^8$ *Chlamydia pneumoniae* and fed different diets

| Protein/Arginine content of diet | Disease severity (% lung weight increase) |
| --- | --- |
| 12%–0.5% | 80.56 |
| 14%–0.7% | 66.28 |
| 16%–0.9% | 67.46 |
| 18%–1.1% | 59.72 |
| 20%–1.3% | 59.12 |

The data in Table 1 suggest that there is a dependency of disease outcome on protein/arginine content of the diet, with enhanced disease resulting where A/J mice are fed low amounts of protein and arginine. These results indicate that in low responder mice such as A/J mice, low amounts of both arginine and protein in diet might result in arginine levels too low to support physiological functions of the immune response. However, these results also indicate that higher levels of both nutrients do support physiological functions of the immune response.

Based on these results, we tested disease outcomes under different levels of arginine and protein nutrition. The first experiment involved a test of recall response. Typically, mice exposed to a low inoculum of *Chlamydia pneumoniae* exhibit protective immunity when the mice are challenge-inoculated 4 weeks later. Groups of 6-week old female A/J mice were either live-vaccinated with an intranasal inoculation of $5\times10^5$ inclusion forming units (IFU; infectious organisms) *Chlamydia pneumoniae* or were mock-exposed (control). Beginning two weeks later, all mice were fed a diet containing 14% protein/0.8% arginine. After two weeks on this diet, all mice were intranasally challenged with $3.5\times10^8$ IFU *C. pneumoniae* and sacrificed 7 days later. Disease severity was assessed by percent lung weight increase and by a determination of total *C. pneumoniae* genomes per lung. The results are shown in Table 2.

TABLE 2

Recall response in day-7 disease of female A/J mice live-vaccinated with $5 \times 10^5$ IFU *Chlamydia pneumoniae* or mock-vaccinated

| 14% protein - 0.8% arginine diet | Live-vaccinated A/J mice | Naïve control A/J mice |
| --- | --- | --- |
| % lung weight increase | 130.8% | 53.1% |
| Log$_{10}$ *C. pneumoniae* genomes/lung | 533 | 7.16 |

The data in Table 2 demonstrate that disease severity is significantly different in live-vaccinated versus naïve mice as measured both by lung weight increases and logarithm of total *Chlamydia pneumoniae* genomes per lung (p=0.012 and 0.018, respectively). However, although live-vaccinated mice had about 100-fold fewer chlamydial genomes per lung than naïve mice, they suffered a much higher severity of disease. In fact, several of the live-vaccinated mice died on days 6 and 7 after challenge inoculation, while none of the naïve mice died. While the invention is not bound by any particular mechanism of the progression of chlamydial disease, this discrepancy between lung disease and chlamydial lung burden suggests that in the live-vaccinated mice, a protective immune response eliminated chlamydiae but was not effective enough to avoid profound proliferation of Chlamydia-specific T cells and infiltration of lung tissue by these cells. The infiltration of lung tissue by mononuclear cells (T cells and macrophages) is a hallmark of chlamydial interstitial pneumonia and causes mortality by disabling lung contraction. This result indicates that a low arginine/protein diet might result in insufficient production of NO by macrophages, which could partially disable the effector arm of the immune response and result in a corresponding hyperproliferation of immune cells and enhanced interstitial pneumonia.

These results indicate that use of mice with low macrophage inflammatory response in chlamydial challenge infections requires a diet containing high amounts of arginine and/or protein to maximally enable the immune response in these mice during a vaccine immune recall experiment. We evaluated this assessment in another live-vaccine experiment using a diet containing 24% protein-1.7% arginine. Forty-five female 6 week old A/J mice were intranasally inoculated with $1 \times 10^6$ Chlamydia pneumoniae organisms as live vaccine, and 39 mice were mock live-vaccinated. After 2 weeks, all mice were put on a 24% protein-1.7% arginine diet. Four weeks after live vaccination, the mice were intranasally challenged with $1 \times 10^8$ Chlamydia pneumoniae organisms and sacrificed 10 days later. Results of this experiment are listed in Table 3.

TABLE 3

Day-10 disease in female A/J mice live- or mock-vaccinated and subsequently inoculated with Chlamydia pneumoniae

| 24% protein - 1.7% arginine diet | Live-vaccinated A/J mice | Naïve control A/J mice |
|---|---|---|
| % lung weight increase | 32.99% | 46.19% |
| Log 10 C. pneumoniae genomes/lung | 4.16 | 6.33 |

The results shown in Table 3 confirm that a low protein-arginine diet fed to low macrophage inflammatory responder mice is detrimental during challenge inoculation of vaccinated mice. With a high protein-arginine diet, the disease and chlamydial lung burden responses of both naïve and live-vaccinated animals were parallel, showing an association of enhanced elimination of chlamydiae with protection from lung disease (p=0.001 and 0.000 for differences in lung weight increase and log chlamydial lung burden, respectively). Thus, during immune recall challenge with Chlamydia, the immune response of low macrophage inflammatory responder mice is maximally enabled by feeding mice a high protein-arginine diet.

Example 3

Cryostaining and Analysis of Infected Lung Tissue

Both C57BL/6 and BALB/c mouse strains produced NO by NOS2 expressed in Chlamydia-infected macrophages (results shown in FIG. 4). Mice infected with $8.2 \times 10^5$ IFU C. psittaci were sacrificed on day 12 (panels A and E; maximum disease) or day 4 (panels B–D and F–H; maximum innate response). Lungs of infected mice were infused with 2% paraformaldehyde and processed using paraffin or infused with OCT and snap-frozen. Deparaffinized sections (4 μm) were stained with hematoxylin and eosin. Immunohistochemical staining was performed on deparaffinized or acetone-fixed frozen sections with polyclonal rabbit antibodies against *C. psittaci* B577 or a C-terminal peptide of murine NOS2 (Calbiochem) and on cryosections with rat mAb against mouse F4/80 antigen (Serotec). Bound antibodies were detected with goat anti rabbit Ig-peroxidase or goat anti-rat Ig-peroxidase and diaminobenzidine and Nova-Red chromogen substrates (Vector Laboratories). Paraformaldehyde-fixed tissue sections showed a better preservation of tissue structure than cryosections. Distribution of target antigens in double-immunostained cryosections was highly colocalized, such that discrete resolution of color precipitates could not be observed at low magnification or in print.

Panels A and E of FIG. 4 show hematoxylin and eosin staining of lungs of mice sacrificed on day 12 (magnification, ×100). Lungs of BALB/c mice (A) appeared essentially normal with minor diffuse interstitial and few small foci of peribronchiolar mononuclear cell infiltrate. In contrast, lungs of C57BL/6 mice (E) showed extensive mononuclear cell infiltrates and large areas of lung consolidation. Panels B, C, F, and G of FIG. 4 show serial sections of lung from day 4 with foci of mononuclear infiltrates from BALB/c mice (B and C; magnification, ×100) and C57BL/6 mice (F and G; magnification, ×400). These sections were stained for *C. psittaci* (B and F) or NOS2 (C and G). Chlamydial antigen and NOS2 colocalized to cells of macrophage morphology in both mouse strains. These cells of macrophage morphology were positive for macrophage maturation antigen F4/80 in cryosections (D and H), and antibodies that recognize chlamydiae or NOS2 colocalized with the F4/80 antigen. Panels D and H of FIG. 4 show cryosections (magnification ×1,000) of lung inflammatory foci of BALB/c (D) and C57BL/6 mice (H) double-immunostained for *C. psittaci* and F4/80 macrophage maturation antigen; *C. psittaci* staining and F8/80 staining colocalized. Double-immunostaining of cryosections for NOS2 and F4/80 or for *C. psittaci* and NOS2 resulted in virtually identical patterns of distribution.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed:

1. A method of evaluating the efficacy of a therapeutic or prophylactic treatment of *Chlamydia*-induced disease, comprising the steps of:
   a) rationally selecting a particular mouse strain and identifying whether said strain is a low nitric oxide (NO) responder strain or a high NO responder strain when said strain is exposed to bacterial antigens;
   b) rationally selecting a dose of *Chlamydia* to be administered to a test mouse of said strain;
   c) if said mouse strain is a low nitric oxide responder, rationally selecting a feeding regimen with high levels of arginine and feeding said test mouse according to said regimen, and if said mouse strain is a high nitric oxide responder, performing at least one step selected from the group consisting of:
      (i) rationally selecting a feeding regimen with low levels of arginine and feeding said test mouse according to said regimen; and
      (ii) treating said test mouse with an inhibitor of nitric oxide synthase-2 (NOS2);
   d) administering said dose of *Chlamydia* to said test mouse;
   e) administering said therapeutic or prophylactic treatment to said test mouse; and
   f) assessing the severity of chlamydial disease in said test mouse.

2. The method of claim 1, wherein said treatment is a prophylactic treatment and said step of administering said prophylactic treatment is performed before said step of administering *Chlamydia* to said mouse.

3. The method of claim 1, wherein the step of administering *Chlamydia* to said mouse comprises administering between $1 \times 10^5$ and $1 \times 10^6$ IFU of *Chlamydia* to said mouse intranasally.

4. The method of claim 1, wherein said mouse strain is A/J.

5. The method of claim 4, wherein the step of rationally selecting a feeding regimen comprises selecting a diet high in protein and arginine.

6. The method of claim 1, wherein the step of rationally selecting a dose of *Chlamydia* to be administered to said test mouse comprises evaluating the mouse strain from which said test mouse is selected to determine the $LD_{50}$ for said mouse strain when treated with *Chlamydia psittaci*.

* * * * *